United States Patent
Wu et al.

(10) Patent No.: US 8,914,119 B2
(45) Date of Patent: Dec. 16, 2014

(54) ELECTRICAL BRAIN THERAPY PARAMETER DETERMINATION BASED ON A BIOELECTRICAL RESONANCE RESPONSE

(75) Inventors: Jianping Wu, Shoreview, MN (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 271 days.

(21) Appl. No.: 13/447,685

(22) Filed: Apr. 16, 2012

(65) Prior Publication Data
US 2012/0271375 A1 Oct. 25, 2012

Related U.S. Application Data

(60) Provisional application No. 61/477,325, filed on Apr. 20, 2011.

(51) Int. Cl.
*A61N 1/00* (2006.01)
*A61N 1/36* (2006.01)

(52) U.S. Cl.
CPC ........ *A61N 1/36139* (2013.01); *A61N 1/36067* (2013.01); *A61N 1/36171* (2013.01); *A61N 1/36153* (2013.01); *A61N 1/36185* (2013.01)
USPC .................................... 607/45; 607/2; 607/1

(58) Field of Classification Search
CPC ........... A61N 1/36082; A61N 1/36067; A61N 1/36025
USPC ................................................ 607/45, 2, 3, 1
See application file for complete search history.

(56) References Cited

U.S. PATENT DOCUMENTS

| 4,227,516 | A | 10/1980 | Meland et al. |
|---|---|---|---|
| 4,753,246 | A | 6/1988 | Freeman |
| 4,776,345 | A | 10/1988 | Cohen et al. |
| 5,299,569 | A | 4/1994 | Wernicke et al. |
| 6,157,857 | A | 12/2000 | Dimpfel |
| 6,167,298 | A | 12/2000 | Levin |
| 6,200,273 | B1 | 3/2001 | Sininger |

(Continued)

FOREIGN PATENT DOCUMENTS

| WO | 2006034305 A2 | 3/2006 |
|---|---|---|
| WO | 2010014686 A1 | 2/2010 |
| WO | 2010039274 A1 | 4/2010 |

OTHER PUBLICATIONS

Loddenkkemper, et al., "Circadian Patterns of Pediatric Seizures," Neurology 76, Jan. 11, 2011: 145-153.

(Continued)

*Primary Examiner* — Christopher D Koharski
*Assistant Examiner* — Philip Edwards
(74) *Attorney, Agent, or Firm* — Beth L. McMahon

(57) ABSTRACT

Various methods and apparatuses are disclosed that concern delivering electrical stimulation to a brain at a plurality of different stimulation frequencies, sensing one or more bioelectrical signals, and identifying a bioelectrical resonance response of the brain to the electrical stimulation. The bioelectrical resonance response may be identified based on a parameter of oscillation of the one or more bioelectrical signals and indicative of resonance of an area of the brain to one stimulation frequency of the plurality of stimulation frequencies. A stimulation frequency parameter for a therapy may be set based on the identified bioelectrical resonance response, wherein the stimulation frequency parameter is set at or near the one stimulation frequency.

34 Claims, 5 Drawing Sheets

(56) References Cited

U.S. PATENT DOCUMENTS

| | | |
|---|---|---|
| 6,227,203 B1 | 5/2001 | Rise et al. |
| 6,402,520 B1 | 6/2002 | Freer |
| 6,453,193 B1 | 9/2002 | Heyrend et al. |
| 6,615,076 B2 | 9/2003 | Mitra |
| 6,920,351 B2 | 7/2005 | Mitra |
| 7,006,872 B2 | 2/2006 | Gielen et al. |
| 7,089,059 B1 | 8/2006 | Pless |
| 7,120,486 B2 | 10/2006 | Leuthardt |
| 7,171,339 B2 | 1/2007 | Repucci |
| 7,257,439 B2 | 8/2007 | Llinas |
| 7,280,867 B2 | 10/2007 | Osorio et al. |
| 7,341,562 B2 | 3/2008 | Pless |
| 7,392,079 B2 | 6/2008 | Donoghue |
| 7,409,321 B2 | 8/2008 | Repucci |
| 7,532,935 B2 | 5/2009 | Maschino et al. |
| 7,577,472 B2 | 8/2009 | Li et al. |
| 7,626,015 B2 | 12/2009 | Feinstein |
| 7,668,591 B2 | 2/2010 | Lee et al. |
| 7,734,340 B2 | 6/2010 | DeRidder |
| 7,747,318 B2 | 6/2010 | John |
| 7,801,601 B2 | 9/2010 | Maschino et al. |
| 7,818,065 B2 | 10/2010 | Llinas |
| 7,819,812 B2 | 10/2010 | John |
| 7,892,182 B2 | 2/2011 | Pless |
| 7,894,890 B2 | 2/2011 | Sun et al. |
| 7,894,903 B2 | 2/2011 | John |
| 7,937,138 B2 | 5/2011 | Liley |
| 8,017,764 B2 | 9/2011 | Feinstein |
| 8,073,534 B2 | 12/2011 | Low |
| 8,078,281 B2 | 12/2011 | Foffani |
| 8,090,674 B2 | 1/2012 | Ginosar |
| 8,140,152 B2 | 3/2012 | John |
| 2001/0003145 A1 | 6/2001 | Mori et al. |
| 2004/0073129 A1 | 4/2004 | Caldwell et al. |
| 2004/0073273 A1 | 4/2004 | Gluckman et al. |
| 2005/0033154 A1 | 2/2005 | deCharms |
| 2005/0154424 A1 | 7/2005 | Tass |
| 2005/0197560 A1 | 9/2005 | Rao et al. |
| 2005/0209512 A1 | 9/2005 | Heruth et al. |
| 2005/0215884 A1 | 9/2005 | Greicius et al. |
| 2005/0283053 A1 | 12/2005 | deCharms |
| 2006/0155348 A1 | 7/2006 | deCharms |
| 2006/0173259 A1 | 8/2006 | Flaherty |
| 2006/0212090 A1 | 9/2006 | Lozano et al. |
| 2007/0067003 A1 | 3/2007 | Sanchez |
| 2007/0123758 A1 | 5/2007 | Miesel et al. |
| 2007/0142874 A1* | 6/2007 | John ............... 607/45 |
| 2007/0167991 A1 | 7/2007 | DiLorenzo |
| 2007/0191704 A1 | 8/2007 | deCharms |
| 2007/0213783 A1 | 9/2007 | Pless et al. |
| 2007/0225674 A1 | 9/2007 | Molnar et al. |
| 2007/0244407 A1 | 10/2007 | Osorio |
| 2008/0001600 A1 | 1/2008 | deCharms |
| 2008/0015459 A1 | 1/2008 | Llinas |
| 2008/0045775 A1 | 2/2008 | Lozano |
| 2008/0071150 A1 | 3/2008 | Miesel et al. |
| 2008/0077039 A1 | 3/2008 | Donnett |
| 2008/0243022 A1 | 10/2008 | Donnett |
| 2008/0269631 A1 | 10/2008 | Denison et al. |
| 2009/0082691 A1 | 3/2009 | Denison et al. |
| 2009/0099623 A1 | 4/2009 | Bentwich |
| 2009/0099627 A1 | 4/2009 | Molnar et al. |
| 2009/0105521 A1 | 4/2009 | Bentwich |
| 2009/0124919 A1 | 5/2009 | Ginosar et al. |
| 2009/0163982 A1 | 6/2009 | deCharms |
| 2009/0177144 A1 | 7/2009 | Masmanidis |
| 2009/0179642 A1 | 7/2009 | deCharms |
| 2009/0192556 A1 | 7/2009 | Wu et al. |
| 2009/0196471 A1 | 8/2009 | Goetz |
| 2009/0220425 A1 | 9/2009 | Moxon |
| 2009/0318794 A1 | 12/2009 | deCharms |
| 2009/0318826 A1 | 12/2009 | Green et al. |
| 2010/0069739 A1 | 3/2010 | deCharms |
| 2010/0100153 A1 | 4/2010 | Carlson |
| 2010/0114237 A1 | 5/2010 | Giftakis et al. |
| 2010/0121213 A1 | 5/2010 | Giftakis |
| 2010/0121214 A1 | 5/2010 | Giftakis |
| 2010/0121215 A1 | 5/2010 | Giftakis |
| 2010/0135553 A1 | 6/2010 | Joglekar |
| 2010/0137937 A1 | 6/2010 | John et al. |
| 2010/0241020 A1 | 9/2010 | Zaidel et al. |
| 2010/0262205 A1 | 10/2010 | DeRidder |
| 2010/0280334 A1 | 11/2010 | Carlson et al. |
| 2010/0280335 A1 | 11/2010 | Carlson et al. |
| 2010/0280336 A1 | 11/2010 | Giftakis et al. |
| 2010/0280403 A1 | 11/2010 | Erdogmus |
| 2010/0286748 A1 | 11/2010 | Midani |
| 2011/0105584 A1 | 5/2011 | Feinstein et al. |
| 2011/0130797 A1 | 6/2011 | Talathi et al. |
| 2011/0137371 A1 | 6/2011 | Giftakis et al. |
| 2011/0144716 A1 | 6/2011 | Bikson et al. |
| 2011/0184489 A1 | 7/2011 | Nicolelis et al. |
| 2011/0196446 A1 | 8/2011 | Wu et al. |
| 2011/0218454 A1 | 9/2011 | Low |
| 2011/0257715 A1 | 10/2011 | Jarosh et al. |

OTHER PUBLICATIONS

Foffani, et al, "300-HZ Subthalamic Oscillations in Parkinson's Disease", Brain, 2003, pp. 2153-2163, vol. 126, No. 10, Advanced Access Publication.

International Search Report and Written Opinion, Aug. 29, 2012, PCT/US2012/033750.

Zaehle, et al, "Resonance Phenomena in the Human Auditory Cortex: Individual Resonance Frequencies int eh Cerebral Cortex Determine Electrophysiological Responses", Experimental Brain Research, 2010, pp. 629-635, vol. 203.

Eusebio, et al., "Resonance in Subthalamo-Cortical Circuits in Parkinson's Disease", Brain 2009, pp. 1-12.

Garrett et al., The Importance of Being Variable, The Journal of Neuroscience, Mar. 23, 2011, 31(12): 4496-4503.

Keimel et al., "Development Proposal: A Low Cost System for fMRI and Spectroscopic Screening and Monitoring of Alzheimer's Disease", Advanced Function Biomedical Imaging, University of Minnesota, Fall 2008, Dec. 12, 2008.

Lynall et al., "Functional Connectivity and Brain Networks in Schizophrenia", J. Neuroscience, Jul. 14, 2010—30(28):9477-9487.

Pihlajamaki et al., "Functional MRI Assessment of Task-Induced Deactivation of the Default Mode Network in Alzheimer's Disease and At-Risk Older Individuals," Behavioral Neurology 21 (1) (2009) 77-91.

Sperling, et al., "Functional Alterations in Memory Networks in Early Alzheimer's Disease," Neuromol Med (2010) 12:27-43.

Van Veen, et al., "Localization of Brain Electrical Activity via Linearly Constrained Minimum Variance Spatial Filtering" IEEE Transactions on Biomedical Engineering, vol. 44, No. 9, Sep. 1997.

Westlye, et al., "Increased Hippocampal Default Mode Synchronization During Rest in Middle-Aged and Elderly APOE ϵ4 Carriers: Relationships with Memory Performance," The Journal of Neuroscience, May 25, 2011, 31(21): 7775-7783.

* cited by examiner

ELECTRICAL BRAIN THERAPY PARAMETER DETERMINATION BASED ON A BIOELECTRICAL RESONANCE RESPONSE

PRIORITY

This application claims the benefit of U.S. Provisional Application No. 61/477,325 entitled "ELECTRICAL THERAPY PARAMETER DETERMINATION BASED ON A BIOELECTRICAL RESONANCE RESPONSE" and filed Apr. 20, 2011, the entire contents of which are incorporated herein by reference.

TECHNICAL FIELD

The disclosure relates to medical systems, and, more particularly, medical systems that deliver an electrical therapy to a patient's brain.

BACKGROUND

Implantable medical devices, such as electrical stimulation devices, may be used in different therapeutic applications, such as fir deep brain stimulation, spinal cord stimulation, pelvic stimulation, gastric stimulation, peripheral nerve stimulation, or functional electrical stimulation of a target tissue site within a patient. An electrical stimulation device may be used to treat a variety of symptoms or conditions of a patient, such as chronic pain, tremor, Alzheimer's disease, Parkinson's disease, other types of movement disorders, seizure disorders (e.g., epilepsy), urinary or fecal incontinence, sexual dysfunction, obesity, mood disorders, gastroparesis, or diabetes. In some therapy systems, an implantable electrical stimulator delivers electrical therapy to a target tissue site within a patient with the aid of one or more electrodes, which may be deployed by medical leads.

SUMMARY

In general, the disclosure relates to methods, systems, and devices for identifying a stimulation frequency parameter that evokes a biodectrical resonance response of an area of a patient's brain.

Various embodiments concern a method for configuring therapy, comprising: delivering electrical stimulation to a brain at a plurality of different stimulation frequencies; sensing one or more bioelectrical signals; identifying a bioelectrical resonance response of the brain to the electrical stimulation, the bioelectrical resonance response identified based on a parameter of oscillation of the one or more bioelectrical signals and indicative of resonance of an area of the brain to one stimulation frequency of the plurality of stimulation frequencies; setting a stimulation frequency parameter for a therapy based on the identified bioelectrical resonance response, wherein the stimulation frequency parameter is set at or near the one stimulation frequency; and delivering the therapy to the brain using the set stimulation frequency parameter. In some cases, each of delivering electrical stimulation, sensing, identifying, setting, and delivering the therapy are performed at least in part by control circuitry. Some of the embodiments include delivering the electrical stimulation for each of a plurality of stimulation intervals, the electrical stimulation being delivered for each stimulation interval of the plurality at a respective stimulation frequency of the plurality of different stimulation frequencies.

In some of the embodiments, the parameter of oscillation comprises a duration of a bioelectrical oscillation response to the electrical stimulation; and identifying the bioelectrical resonance response comprises determining which stimulation frequency of the plurality of different stimulation frequencies is associated with the longest duration of bioelectrical oscillatory response. In some of the method embodiments, the parameter of oscillation comprises a power value in the frequency domain; and identifying the bioelectrical resonance response comprises determining which stimulation frequency of the plurality of different stimulation frequencies is associated with the highest power value. In some of the method embodiments, the electrical stimulation is delivered to subthalamic nucleus, and the area of the brain for which the bioelectrical resonance response is identified is the subthalamic nucleus. In some cases, the therapy is delivered to treat a movement disorder. In some cases, the plurality of different stimulation frequencies comprise a range of frequencies within the gamma frequency band.

In some cases, setting the stimulation frequency parameter for the therapy comprises setting the stimulation frequency parameter at the one stimulation frequency. In some cases, setting the stimulation frequency parameter near the one stimulation frequency comprises setting the stimulation frequency parameter closer to the one stimulation frequency than to any other stimulation frequency of the plurality of different stimulation frequencies.

In various embodiments, delivering electrical stimulation to the brain at the plurality of different stimulation frequencies comprises delivering electrical stimulation to the brain at the plurality of different stimulation frequencies for each of a plurality of different stimulation amplitude values, and wherein the method further comprises setting a stimulation amplitude parameter of the therapy, the amplitude parameter being set at or slightly higher than the lowest amplitude value of the plurality of different stimulation amplitude values for which the bioelectrical resonance response was identified. In some cases, delivering the electrical stimulation at the plurality of different stimulation frequencies comprises incrementally increasing or decreasing stimulation frequency so as to scan delivery of the electrical stimulation through the plurality of different stimulation frequencies. In some cases, the steps of delivering the electrical stimulation, sensing, identifying the bioelectrical resonance response, and setting the stimulation frequency parameter are repeated according to a schedule or a trigger to update the stimulation frequency parameter. Some embodiments include monitoring for an endogenous bioelectrical oscillation of the patient in a particular frequency band, wherein the steps of delivering the electrical stimulation and identifying the bioelectrical resonance response are preformed based on the endogenous bioelectrical oscillation not being present in the particular frequency band during the monitoring.

Various embodiments concern a system, comprising: means for delivering electrical stimulation to a brain at a plurality of different stimulation frequencies; means for sensing one or more bioelectrical signals; means for identifying a bioelectrical resonance response of the brain to the electrical stimulation, the bioelectrical resonance response identified based on a parameter of oscillation of the one or more bioelectrical signals and indicative of resonance of an area of the brain to one stimulation frequency of the plurality of stimulation frequencies; means for setting a stimulation frequency parameter for a therapy based on the identified bioelectrical resonance response, wherein the stimulation frequency parameter is set at or near the one stimulation frequency; and means for delivering the therapy to the brain using the set stimulation frequency parameter. Such embodiments may further include means for carrying out any technique referenced herein, including the above method steps.

Various embodiments concern a system comprising: one or more sensors configured to receive one or more bioelectrical signals indicative of brain activity; a stimulation generator configured to deliver electrical stimulation to a brain; and control circuitry comprising a processor and memory storing program instructions executable by the processor, the control circuitry configured to: control the stimulation generator to deliver the electrical stimulation to a brain at a plurality of different stimulation frequencies; identify a bioelectrical resonance response of the brain to the electrical stimulation, the bioelectrical resonance response identified based on a parameter of oscillation of the one or more bioelectrical signals and indicative of resonance of an area of the brain to one stimulation frequency of the plurality of stimulation frequencies; set a stimulation frequency parameter for a therapy based on the identified bioelectrical resonance response, the stimulation frequency parameter set at or near the one stimulation frequency; and control the stimulation generator to deliver the therapy to the brain using the set stimulation frequency parameter. In some embodiments, the control circuitry is configured to control the stimulation generator to deliver the electrical stimulation for each of a plurality of stimulation intervals such that the electrical stimulation is delivered for each stimulation interval of the plurality at a respective stimulation frequency of the plurality of different stimulation frequencies.

In some embodiments, the parameter of oscillation comprises a duration of a bioelectrical oscillation response to the electrical stimulation, and wherein the control circuitry is configured to identify the bioelectrical resonance response by determining which stimulation frequency of the plurality of different stimulation frequencies is associated with the longest duration. In some cases, the parameter of oscillation comprises a power value in the frequency domain, and wherein the control circuitry is configured to identify the bioelectrical resonance response by determining which stimulation frequency of the plurality of different stimulation frequencies is associated with the highest power value. In some cases, the therapy comprises a movement disorder therapy. In some cases, the plurality of different stimulation frequencies comprise a range of frequencies within the gamma frequency band.

In some embodiments, the control circuitry is configured to set the stimulation frequency parameter for the therapy at or near the one stimulation frequency by setting the stimulation frequency parameter for the therapy at the one stimulation frequency. In some embodiments, the control circuitry is configured to set the stimulation frequency parameter for the therapy at or near the one stimulation frequency by setting the stimulation frequency parameter closer to the one stimulation frequency than to any other stimulation frequency of the plurality of different stimulation frequencies. In some embodiments, the control circuitry is configured to: control the stimulation generator to deliver electrical stimulation to the brain at the plurality of different stimulation frequencies by controlling the stimulation generator to deliver electrical stimulation to the brain at the plurality of different stimulation frequencies for each of a plurality of different stimulation amplitude values; and set a stimulation amplitude parameter for the therapy by setting the amplitude parameter at or slightly higher than the lowest amplitude value of the plurality of different stimulation amplitude values for which the bioelectrical resonance response was identified.

In various embodiments, the control circuitry is configured to control the stimulation generator to deliver the electrical stimulation at the plurality of different stimulation frequencies by incrementally increasing or decreasing stimulation frequency so as to scan delivery of the electrical stimulation through the plurality of different stimulation frequencies. In various embodiments, the control circuitry is configured to repeat the steps of delivering the electrical stimulation, identifying the bioelectrical resonance response, and setting the stimulation frequency parameter according to a schedule or a trigger to update the stimulation frequency parameter. In some embodiments, the control circuitry is configured to monitor for an endogenous bioelectrical oscillation of the brain in a particular frequency band using the one or more bioelectrical signals, wherein the control circuitry is configured to perform the steps of delivering the electrical stimulation, identifying the bioelectrical resonance response, and setting the stimulation frequency parameter only if the endogenous bioelectrical oscillation is not present in the particular frequency band.

Various embodiments concern a physically embodied computer-readable medium comprising instructions that cause a processor to: deliver electrical stimulation to a brain at a plurality of different stimulation frequencies; sense one or more bioelectrical signals; identify a bioelectrical resonance response of the brain to the electrical stimulation, the bioelectrical resonance response identified based on a parameter of oscillation of the one or more bioelectrical signals and indicative of resonance of an area of the brain to one stimulation frequency of the plurality of stimulation frequencies; set a stimulation frequency parameter for a therapy based on the identified bioelectrical resonance response, wherein the stimulation frequency parameter is set at or near the one stimulation frequency; and deliver the therapy to the brain using the set stimulation frequency parameter.

The details of various examples are set forth in the accompanying drawings and the description below. Other features, objects, and advantages will be apparent from the description and drawings, and from the claims.

DETAILED DESCRIPTION

The methods and apparatuses described herein provide for characterizing a bioelectrical resonance response of a brain and setting stimulation parameters based on the bioelectrical resonance response.

The human brain is composed of billions of neurons interconnected and organized into various areas to perform a variety of functions. The neurons of a particular area can be associated with one or more brain functions. These areas can share networks of neurons. Electrical activation of neurons is the basis for function of brain areas and communication amongst the various brain areas along these networks. It is generally thought that the activation of numerous neurons is necessary to carry out each brain function, such as supporting motor abilities. Moreover, for various areas of the brain, many of the neurons in an area of the brain will depolarize in synchrony in an effort to carry out a function supported by the area. One measure of the level of engagement of an area of the brain is the regularity of the bioelectrical oscillations of the neurons in the area.

Various neurological conditions, such as those associated with injury or disease, can be characterized by abnormal neurological activation patterns. For example, a brain condition associated with some physical manifestation (e.g., tremor) can be characterized by weakened or non-existent oscillatory activity in an area of the brain that would be expected to have certain oscillatory activity under some conditions. In the case of some movement disorders, such as Parkinson's disease, a condition can be characterized by weak or non-existent gamma frequency band oscillations and an abnormally high level of beta band oscillations in the subthalamic nucleus. Stimulation of the subthalamic nucleus with high gamma frequency band pulses can provide some therapeutic results. In the case of deep brain stimulation (DBS) for treating Parkinson's disease, pulses delivered at a predetermined rate (e.g., 130 Hz) can alleviate some of the symptoms associated with Parkinson's disease. However, a stimulation therapy having a predetermined frequency of pulse delivery of 130 Hz may be higher in frequency than what some patients need to experience adequate symptom relief. Lowering of stimulation energy parameters, such as amplitude and stimulation frequency, can be associated with less unintended stimulation, less unneeded stimulation, and/or preservation of battery power.

Figure 1:
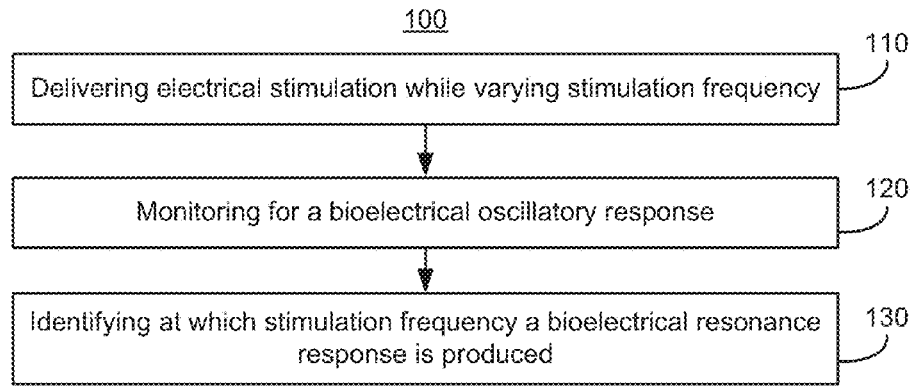
FIG. 1 is a flow diagram for identifying a bioelectrical resonance response stimulation frequency.

The present disclosure concerns customizing electrical stimulation parameters for patients. For each target area of a brain, one or more electrical stimulation parameters are customized based on resonant properties of the target area, as discussed herein, FIG. 1 illustrates a flow chart of a method 100 for recognizing a bioelectrical resonance response of a brain area. The method 100 includes delivering 110 electrical stimulation to a patient's brain while varying the frequency of the stimulation. A continuous series of pulses may be delivered 110 while the frequency of delivery of the pulses is changed throughout the series. In various embodiments, electrical stimulation is delivered 110 at a plurality of different frequencies over a plurality of time intervals, but is delivered 110 at a constant frequency within each time interval. In either manner of delivery 110, the electrical stimulation comprises samples of different stimulation frequencies within a frequency range, such as the gamma frequency range.

Concurrent or intermittent with electrical stimulation delivery 110, the bioelectrical oscillatory response of the brain to the electrical stimulation is monitored 120. Monitoring 120 may include one or more electrodes receiving one or more of a local field potential (LFP), electroencephalogram (EEG), microelectromechanical system (MEMS), magnetoencephalography (MEG), and/or electrocorticographic (ECoG) signal. Monitoring 120 may include processing the signals in some manner (e.g., amplifying, modulating, and filtering) and storing the signals.

Based on the monitoring 120, the stimulation frequency at which a bioelectrical resonance response was produced can be identified 130, if the bioelectrical resonance response was indeed produced. Some areas of the brain will express a bioelectrical resonance response when stimulated with a particular electrical pattern. A bioelectrical resonance response (or a resonant bioelectrical response), as referred to herein, refers to a distinct and pronounced oscillatory response of a neural area, such as an area of the brain, to electrical stimulation having particular delivery parameters including at least a stimulation frequency parameter, and for which similar but different delivery parameters, including stimulation frequency, fail to evoke a similar response. A bioelectrical resonance response of a brain area to stimulation having particular parameters indicates that the brain area is functionally predisposed to activate in an organized way in response to those particular parameters and is not functionally predisposed to respond in the same way to different stimulation parameters. In various cases, the bioelectrical resonance response is characterized by a large increase in specific frequency content of bioelectrical oscillations within a particular frequency range. For example, a brain area may begin to bioelectrically oscillate at 75 Hz when pulses are delivered 110 to the brain area at a particular frequency with a frequency range, but not begin to oscillate at a similar level at 75 Hz or any other frequency when stimulation is delivered at other frequencies of the range. Bioelectrical oscillations of other frequencies may also occur in the brain area before, concurrent, and after the bioelectrical resonant response, but resonance in this case is marked by a significant increase in oscillatory activity (e.g., in the gamma frequency range) in response to stimulation.

A bioelectrical resonance response may manifest in different ways for different brain areas. Therefore, various bioelectrical resonance responses may be recognized for identification 130 of an associated stimulation frequency in several different ways. For example, a signal received as a part of monitoring 120 may be converted to the frequency domain using a fast Fourier transform. A power spectrum may be generated from the signal in the frequency domain, showing the power in the signal at the different oscillation frequencies. The power spectrum may be used to track the signal throughout the delivery 110 of the electrical stimulation over the different stimulation frequencies. If the power spectrum indicates a marked increase in bioelectrical oscillation at a particular frequency when one stimulation frequency is delivered 110, the bioelectrical oscillation not being present or present to a significantly lesser extent during delivery 110 of the other frequencies, then the one stimulation frequency may be identified 130 as the stimulation frequency at which the bioelectrical resonance response is produced.

Various different responses to different stimulation frequencies are possible, including stimulation that does not evoke any sort of response, stimulation that evokes only a disorganized response, stimulation that evokes an organized oscillatory response that lasts only as long as stimulation is delivered, stimulation that evokes an organized oscillatory response that lasts for only a very limited time following cessation of stimulation, and stimulation that evokes an organized oscillatory response that lasts for an extended duration after the electrical stimulation is ended. In the latter case, it is thought that the frequency of stimulation is particularly matched to activate the neural network of the stimulated brain area in a way that the neural network activation continues to be self-supporting for some time. Such extended activation may be used as a biomarker of bioelectrical resonance response, and the stimulation frequency that caused the extended bioelectrical oscillation can be identified 130 as the stimulation frequency that produced the bioelectrical resonance response.

In some embodiments, a bioelectrical resonance response may be recognized for identifying 130 an associated stimulation frequency based on peak amplitudes of the sensed signal (e.g., LFP or EEG) related to each stimulation frequency. For example, if peak amplitudes occur with some recognizable regularity, such as 75 Hz, in response to stimulation at a stimulation frequency of a stimulation frequency range, then in some embodiments it may be concluded that this oscillatory response represents a bioelectrical resonance response if this response does not appear at other stimulation frequencies of a stimulation frequency scan.

In various embodiments, band pass filtering can be used to filter out frequencies that are outside of a targeted range of bioelectrical oscillation, where oscillatory activity indicative of a bioelectrical resonance response inside of the range may be expected. For example, it may be suspected that a bioelectrical resonance response for a particular brain area will include a significant increase in bioelectrical oscillation between 60 and 80 Hz as a biomarker. One or more band pass filters may filter out oscillatory signal content above and below this range, such that an increase in amplitude of a band pass filtered signal indicates increased oscillatory content within this range, and in some cases a resonant bioelectrical response. In some embodiments, multiple band pass filters having different narrow passing ranges can be selectively employed to determine if a signal indicates a change in one of the narrow frequency ranges indicative of a bioelectrical resonance response. For example, one band pass filter may pass 60-62 Hz frequency oscillations, another band pass filter may pass 62-66 Hz frequency oscillations, and other band pass filters incrementing in this fashion may also be used. A signal may be filtered by each of the band pass filters (e.g., in parallel) to see if the bioelectrical signal, when filtered by one of the filters, indicates an increase in amplitude responsive to a particular stimulation pattern, where no increase in amplitude is observed when the signal is filtered by any of the other band pass filters. This can be repeated for other stimulation frequencies to determine whether an amplitude increase is observed within one narrow pass band for a single stimulation frequency, which can indicate that this stimulation frequency evokes the bioelectrical resonance response. In some cases, a bioelectrical resonance response is identified based on an increase in power of a particular frequency (e.g., in a spectrogram) compared to the other frequencies, such that a dominant oscillatory pattern at a particular frequency emerges in response to the electrical stimulation. In some cases, without an increase in the power of a particular single dominant frequency over other frequencies, a bioelectrical resonance response is not identified. However, not all implementations are so limited.

In some cases, monitoring 120 can include starting a timer each time electrical stimulation delivery 110 is stopped after having just delivered stimulation at one of a plurality of frequencies being tested. A signal indicative of oscillatory activity of a targeted brain area can be analyzed (e.g., transformed to the frequency domain, power spectrum determined, and oscillation content compared between different frequencies) to determine if oscillatory activity is present following cessation of stimulation, and if so, how long the oscillatory activity lasts (e.g., the timer stops when the particular oscillatory activity stops entirely or falls below a threshold). The procedure can be repeated for each stimulation frequency of the plurality of stimulation frequencies and the different timer durations for each of these frequencies can be compared to one another. In some embodiments, one stimulation frequency will be identified 130 as the frequency at which a bioelectrical resonance response was produced based on the frequency being associated with the longest timer duration. That is, the stimulation frequency that produces the bioelectrical resonance response is identified 130 based on inducing a longer bioelectrical oscillatory response following stimulation as compared to the other stimulation frequencies of a common frequency range. In some cases, however, none of the stimulation frequencies of a tested range will be considered to have induced a bioelectrical resonance response, despite one frequency being associated with a slightly longer time of bioelectrical oscillation. In some cases, a minimum time threshold may be applied (e.g., the longest time duration of brain area oscillation will have to be at least some minimum duration) and/or the longest duration must be a certain amount or percentage longer than the second longest. Such requirements can ensure that meaningful differences indicative an authentic bioelectrical resonance response are present in the monitored 120 responses before a particular stimulation frequency is identified 130 as producing a bioelectrical resonance response.

It is noted that monitoring 120 the bioelectrical oscillatory response does not mean that such a response will always be present. In many cases a signal being monitored 120 will show little or no oscillatory response during and after stimulation delivery 110, particularly in certain frequency bands, and in such cases no indication of a bioelectrical resonant response is present. In some cases, a bioelectrical response to almost all frequencies of a stimulation frequency range will comprises an erratic signal having little or no oscillatory pattern but one stimulation frequency will cause the stimulated brain area to produce an sinusoidal-type waveform oscillatory pattern. Recognition of such a difference in response to different stimulation frequencies can be the basis for identifying 130 at which stimulation frequency a bioelectrical resonance response is produced by stimulation. In this way, a bioelectrical resonant response can be identified 130 as much by what does not happen at other stimulation frequencies (e.g., no change over to oscillatory activity) as what happens at one stimulation frequency (e.g., organized oscillation is produced). For example, if all stimulation frequencies of a range produce essentially the same oscillatory response (e.g., each having a similar sinusoidal-type waveform pattern), then one stimulation frequency does not standout as producing a bioelectrical resonance response. It is noted that oscillatory activity that is present before stimulation, or present at multiple stimulation frequencies, is not indicative of a bioelectrical resonance response. In particular, it is noted that a bioelectrical resonance response must show some oscillatory change in a bioelectrical signal responsive to delivery 110 of electrical stimulation at a particular frequency that is not present at other stimulation frequencies of a stimulation frequency range.

Signals, including EEG and LFP signals, may exhibit multiple frequency components when converted to the frequency domain, signifying that a brain area may have multiple oscillatory patterns at once. Various techniques can characterize the different oscillatory patterns to identify, among other things, a bioelectrical resonance response. Frequency domain characteristics of each of the sensed bioelectrical brain signal may be determined as absolute values and/or relative values. An example of a frequency domain characteristic may include power level within a particular frequency band. The power level may be determined based on, for example, a spectral analysis of a bioelectrical brain signal. The spectral analysis may indicate the distribution of the power contained in a signal at the different frequencies of a frequency range, based on a finite set of data. In various embodiments, the bioelectrical resonance response may be indicated by which stimulation frequency of a range evoked the highest relative gamma band power. The relative gamma frequency band power may be a ratio of the power in a gamma frequency band of the sensed signal to the overall power of the sensed signal.

Different frequency bands are associated with different activities in the brain. In various embodiments, a scan of stimulation frequencies will only use a plurality of stimulation frequencies within a particular frequency band, such as the gamma frequency band, and may further only monitor 120 for a bioelectrical oscillatory response in the same frequency band, such that the bioelectrical resonance response must oscillate within the scanned stimulation frequency spectrum. One example of the frequency bands that can be used is shown in Table 1:

TABLE 1

| Frequency (f) Band Hertz (Hz) | Frequency Information |
|---|---|
| f < 4 Hz | δ (delta frequency band) |
| 4 Hz ≤ f ≤ 8 Hz | theta frequency band |
| 8 Hz ≤ f ≤ 13 Hz | α (alpha frequency band) |
| 13 Hz ≤ f ≤ 35 Hz | β (beta frequency band) |
| 35 Hz ≤ f ≤ 100 Hz | γ (gamma frequency band) |
| 100 Hz ≤ f ≤ 200 Hz | high γ (high gamma frequency band) |

Stimulation of an area of the brain at the frequency for which the area exhibits a bioelectrical resonance response may provide for effective therapeutic results in treating various diseases. Furthermore, customizing a stimulation frequency parameter for a patient having Parkinson's disease, instead of delivering therapy at a predetermined frequency (e.g., 130 Hz), may lower energy consumption to save on device battery life and minimize unintended stimulation. Some patients may receive more relief from disease symptoms through stimulation parameters individually customized based on bioelectrical resonance response and in some cases may experience fewer side effects as compared to predetermined non-customized parameters.

Figure 2:
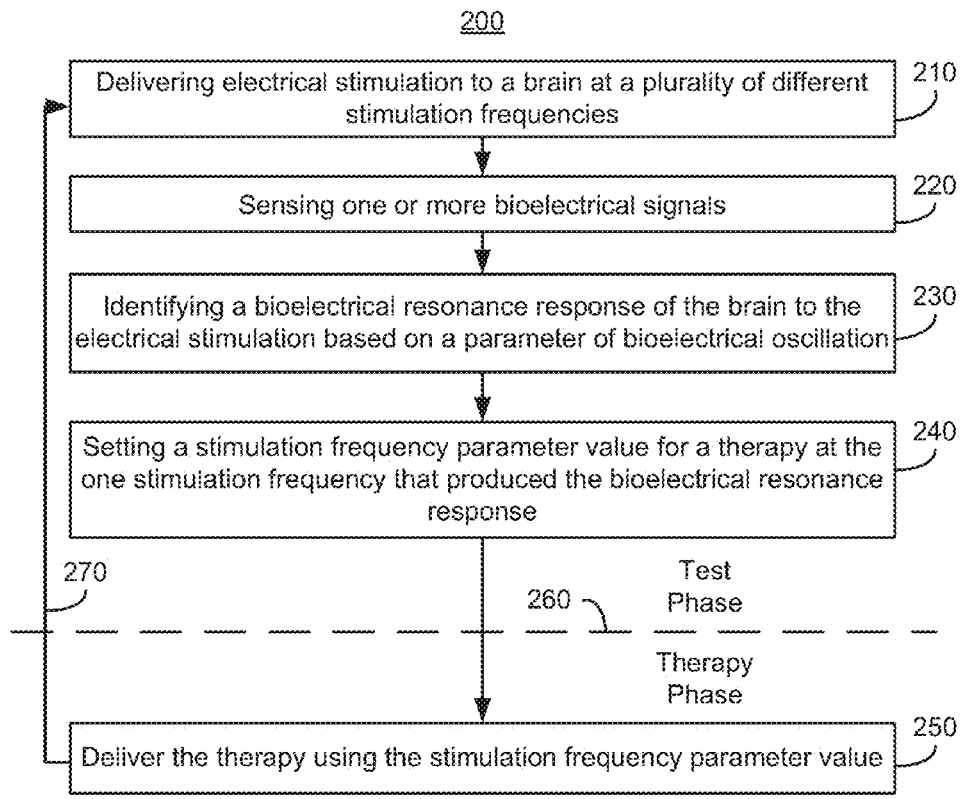
FIG. 2 is a flow diagram for setting a stimulation parameter based on a bioelectrical resonance response.

FIG. 2 illustrates a flow chart of a method 200 for establishing a stimulation frequency parameter of a therapy. The method 200 includes delivering 210 electrical stimulation to a patient's brain at a plurality of different stimulation frequencies. The stimulation frequencies are delivered in different time intervals so as to test each simulation frequency individually, although the time intervals may be consecutive or intermittent. The plurality of different stimulation frequencies can evenly span within a frequency range, such as 60-100 Hz. The stimulation frequencies of the plurality may be scanned as incrementing integer values (e.g., 60 Hz, 61 Hz, 62 Hz, etc.) or other pattern (e.g., decrementing by 0.3 Hz, from 100 Hz to 60 Hz).

Continuous or intermittent with stimulation delivery 210, one or more bioelectrical signals can be sensed 220. As discussed herein, a bioelectrical resonance response of the brain to the electrical stimulation can be identified 230 based on a parameter of bioelectrical oscillation of the one or more signals. For example, a significant increase in the power level of one frequency of a frequency spectrum as compared to power levels of the other frequencies of the frequency spectrum for each of the other stimulation frequencies of the plurality of different stimulation frequencies can indicate that the one frequency caused a bioelectrical resonance response in a targeted area of the brain if this increase was not observed with other stimulation frequencies. In this and other ways, delivering 210, sensing 220, and identifying 230 steps can recognize which one stimulation frequency parameter value out of a range of stimulation frequency parameter values is matched to cause a bioelectrical resonance response in a brain area. A stimulation frequency parameter value for a therapy can then be set 240 at the one stimulation frequency that produced the bioelectrical resonance response.

Setting 240 the stimulation frequency parameter can include programming control circuitry of an implantable medical device to deliver a therapy at the one stimulation frequency for later delivery. In this way, the delivering 210, sensing 220, identifying 230, and setting 240 steps can form a testing phase and later delivery 250 of a therapy that uses the one stimulation frequency parameter value can form a therapy phase, a transition 260 existing between the two phases. The two phases are distinct in several ways, including that the testing phase is not intended to therapeutically treat a brain condition and indeed the scan in the test phase means that most electrical stimulation delivered in the test phase will not cause the bioelectrical resonance response while the therapy phase is focused exclusively on delivering 250 stimulation using a single frequency parameter recognized to cause the bioelectrical resonance response.

A device having control circuitry configured to carry out the method 200 may be configured to transition 260 between the test and therapy phases. As discussed further herein, several events can cause control circuitry to exit the therapy phase and transition 260 back to the test phase to perform the delivering 210, sensing 220, identifying 230, and setting 240 steps again (as show by loop 270) before the device reenters the therapy phase with an updated stimulation frequency parameter setting 240. Conditions to reenter the test phase from the therapy phase can occur according to a schedule (e.g., periodically, such as once per day), based on a user input (e.g., patient or clinician provides an input indicating the presence of symptoms), and/or by automatic detection of a condition (e.g., lack of detection of the bioelectrical resonance response, detection of problematic brain activity, and/or detection of physical symptoms of the condition being treated). Such implementations are further discussed in connection with FIG. 4.

Figure 3:
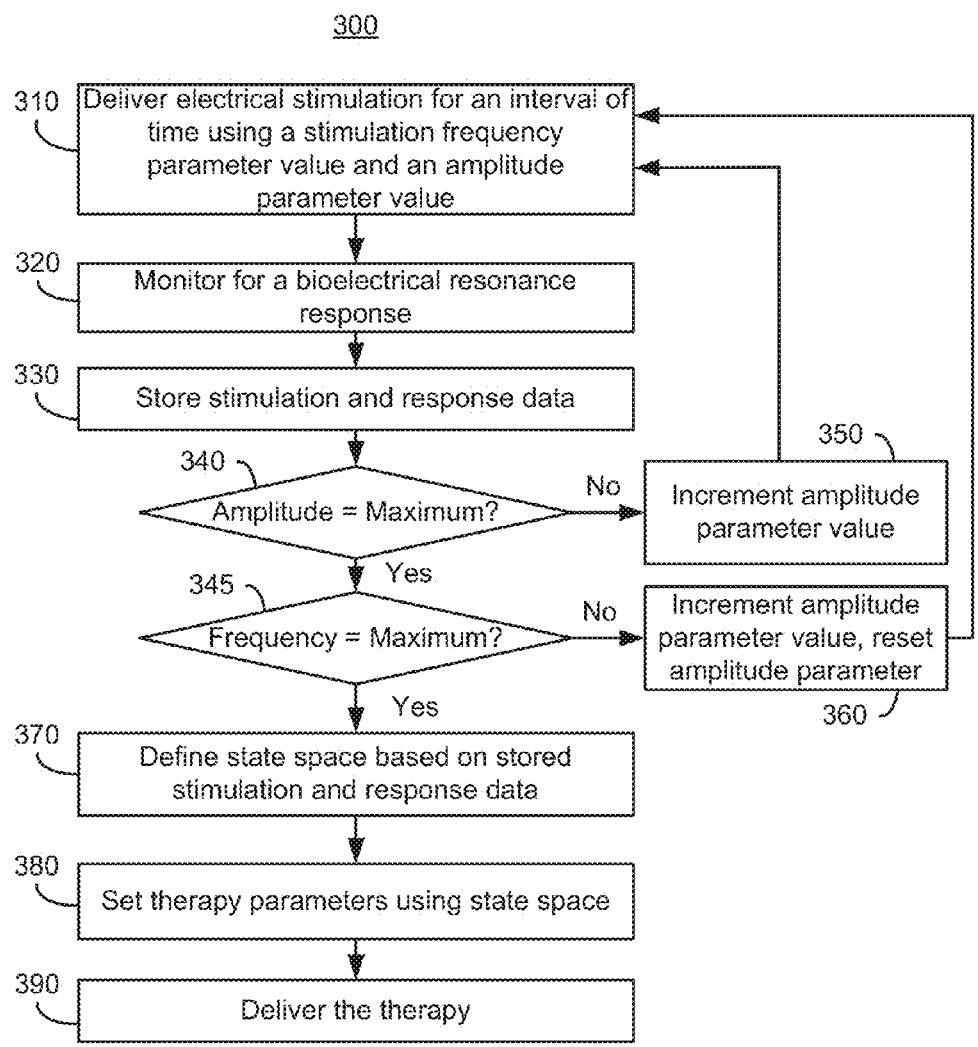
FIG. 3 is a flow diagram for defining stimulation state space based on a bioelectrical resonance response.

FIG. 3 illustrates a flow diagram of a method 300 for scanning through multiple different parameters to define a state space. State space, as referred to herein, refers to an atlas of multiple varying stimulation parameters and the response(s) that they evoke. The method 300 includes delivering 310 electrical stimulation for an interval of time using a stimulation frequency parameter value and an amplitude parameter value. Each of the stimulation frequency parameter value and the amplitude parameter value are values of respective ranges (e.g., a frequency range and an amplitude range) and preferably are the lowest values within the respective ranges for the initial conditions of the method 300. Delivery 310 for each combination of a stimulation frequency parameter value and an amplitude parameter value occurs for an interval of time which may be in the range of milliseconds (e.g., 500), seconds (e.g., 5), or minutes (e.g., 2), although other values are contemplated as well. Concurrent and/or following delivery 310, the method 300 monitors 320 for an oscillatory bioelectrical response. Monitoring 320 may be performed in any manner referenced herein, including generating a frequency power spectrum for each different stimulation frequency, measuring the frequency of signal peaks, and/or alternating periods of stimulation and no stimulation to recognize whether a signal amplitude and/or power level change indicates the presence of a bioelectrical resonance response to electrical stimulation.

Concurrent and/or following monitoring 320, stimulation and response data is stored 330 in memory. Storing 330 may include storing a record of the parameter values used for a particular interval and sensed data regarding any evoked responses, possibly including a determined frequency spectrum plot and/or other indication of a bioelectrical resonance response. Storing 330 may include storing raw or processed bioelectrical signals, frequency spectrums plots, and/or power levels, among other characteristics.

The method 300 includes determining whether the amplitude parameter value used in delivery 310 in the current iteration loop (i.e. for latest time interval) is at a maximum value 340 of a predefined range. The range may be predefined as a default setting or a customized range, the range outlining the acceptable range of stimulation amplitude. The lower end of the range may be where a meaningful evoked response is unlikely and the higher end of the range may be the limit of acceptable stimulation without undue unintended stimulation (e.g., to tissue areas neighboring the target tissue). It is expected that if the method 300 starts at low initial conditions than multiple iterations will be required before the amplitude parameter value is at a maximum value 340, and until then, the amplitude parameter value will be incremented 350 for each iteration loop and the method 300 will continue with delivering 310 electrical stimulation for another interval of time using the previous stimulation frequency parameter value and the incremented 350 amplitude parameter value. In this way, the method 300 can loop through delivering 310, monitoring 320, storing 330, and incrementing 350 for multiple intervals of time using a different combination of stimulation parameters for each interval until the scan reaches the maximum amplitude value 340 for a current stimulation frequency, at which point the method 300 checks whether the frequency is at the maximum value.

The method 300 includes determining whether the stimulation frequency parameter value used in delivery 310 in the present iteration loop is at a maximum value 345 of a predefined range. As with stimulation amplitude, the frequency range may be predefined as a default setting (e.g., the gamma frequency range) or a customized range, the range outlining the outer bounds of likelihood of finding a therapeutic bioelectrical resonance response. As with the amplitude loop, it is expected that if the method 300 starts at low initial conditions, than multiple iterations will be required before the frequency parameter value is at a maximum value 345, and until then, the stimulation frequency amplitude value will be scanned through the full amplitude range for each stimulation frequency increment 360 for each iteration and interval of time. Resetting the amplitude parameter value to the lowest level of the amplitude parameter range with each stimulation frequency increment 360 means the amplitude range will be scanned from lowest to highest before the maximum amplitude test 340 is again passed and the method 300 increments 360 to the next frequency value, until the maximum frequency 345 is reached as well. In this way, the method 300 can loop through delivering 310, monitoring 320, storing 330, and incrementing 360 the stimulation frequency and incrementing 350 the amplitude until the scan is performed through each combination of stimulation frequency and stimulation amplitude of the respective frequency and amplitude ranges over a plurality of time intervals.

In some cases, it is expected that at lower amplitude levels a bioelectrical resonance response will not be evoked by any of the stimulation frequencies. At higher amplitude scans however, a frequency that evokes the bioelectrical resonance response may emerge. At even higher stimulation amplitudes, the bioelectrical resonance response may disappear (even though the same stimulation frequency that produced a bioelectrical resonance response at a lower amplitude is used) as the high amplitude may provide a suppressive effect. It is noted, however, that different results are also possible. In any case, the dual scans vary amplitude and frequency delivery parameters over different parameter ranges, wherein the bioelectrical resonance response may be expected at a single stimulation frequency and with one or more stimulation amplitudes within the ranges. While the method 300 of FIG. 3 first scans through an amplitude range for each different frequency, it is contemplated that the order could be changed and a scan through a stimulation frequency range can be performed for each stimulation amplitude increment. Likewise, any other stimulation parameter referenced herein can be scanned additionally or alternatively, such as pulse width and total duration of stimulation in each interval.

Passing both the maximum amplitude 340 and maximum frequency 345 tests indicates that the state space has been scanned and accordingly can be defined 370 based on stored 330 stimulation and response data. Defining 370 the state space may include generating plots or other outputs to present the pattern of evoking the bioelectrical resonance response, which can identify a stimulation frequency and a range of amplitudes that can evoke the bioelectrical resonance response. A bioelectrical resonance response may be recognized as disclosed herein, such as by prolonged oscillatory pattern following stimulation, regular amplitude peaks in a signal, signal amplitude increase following band pass filtering, and/or a change in the power level of a frequency of a frequency spectrum, with the response not being present at other stimulation frequencies of the scanned range.

Based on the state space, therapy parameters can be set 380. The therapy parameters may be static parameters, such as the lowest or second lowest amplitude that caused the bioelectrical resonance response at the one stimulation frequency. In various embodiments, a device may be programmed with a range in which the device can automatically titrate a therapy. For example, a device may be programmed to stimulate using the frequency that is associated with the bioelectrical resonance response and a lower amplitude of the range of the state space identified to evoke the bioelectrical resonance response. If the lower amplitude later becomes ineffective in continuing to evoke the bioelectrical resonance response and/or noticeable symptoms emerge (e.g., tremor), then control circuitry can automatically increase the amplitude within the range of amplitude values for which the state space indicates the bioelectrical resonance response was produced until the bioelectrical resonance response is again recognized, symptoms are controlled, and/or the top of the set 380 amplitude range is reached (in the later case the method 300 may restart to update the state space).

In various embodiments, a stimulation frequency parameter may be set 380 for a therapy at or near the stimulation frequency that was recognized to evoke the bioelectrical resonance response. If the stimulation frequency parameter is set 380 at the stimulation frequency that was recognized to evoke the bioelectrical resonance response, then the same stimulation frequency (e.g., 75 Hz) that evoked a bioelectrical resonance response will be set 380 as the stimulation frequency for the therapy. If the stimulation frequency parameter is set 380 near the stimulation frequency that was recognized to evoke the bioelectrical resonance response, then the stimulation frequency will be set very close to the same stimulation frequency that evoked the bioelectrical resonance response in view of the other stimulation frequencies of any stimulation frequency scans that were performed. For example, if a stimulation frequency scan was performed at increments of 5 Hz, delivering stimulation at 70 Hz, 75 HZ, and 80 Hz, among lower and higher frequencies, and the resonant electrical response appeared at 75 Hz, then setting 380 the stimulation frequency parameter near 75 Hz would mean using a value closer to 75 Hz than to either of 70 Hz and 80 Hz. Setting 380 a stimulation frequency near a tested frequency value allows for further refinement and/or testing at a finer resolution than that already tested to determine an optimal stimulation frequency value.

In various embodiments, a stimulation amplitude parameter may be set 380 for a therapy at or slightly higher than a stimulation amplitude that was recognized to evoke the bioelectrical resonance response. Setting 380 the stimulation amplitude slightly higher than a particular stimulation amplitude that was recognized to evoke the stimulation response can build in some assurance that subsequent stimulation will continue to have enough energy to provoke the bioelectrical resonance response (e.g., in case the tested amplitude sits right at the threshold of causing resonance or patient hydration/cellular chemical concentration alters the threshold), but not so much that the increased amplitude might suppress or washout the desired bioelectrical resonance response.

In various embodiments, scans in the manner of FIG. 3 continue through a range of scanning, such as frequency range scanning, even when a significant change in evoked response activity is recognized, and even if the evoked response within the range is strongly indicative of a resonate bioelectrical response. A reason for this is that if this same change was also observed at other frequencies of additional scanning with a range, then this would indicate that the change is not indeed indicative of the bioelectrical resonance response. As such, various scans of the present disclosure scan through the whole target range regardless of what is sensed within the range. However, in some embodiments, once a stimulation parameter that evokes the resonate bioelectrical response is identified in one stimulation frequency scan, a scan can be performed using only the one stimulation frequency that evoked the bioelectrical resonance response while varying stimulation amplitude across a range.

Various embodiments disclosed herein relate to scanning through stimulation frequency parameters and monitoring for a bioelectrical resonance response. In various embodiments, it is expected that each scan of stimulation frequencies will be within a relatively narrow range, and not comprise the full spectrum of frequencies for which a device may be capable of stimulation. For example, control circuitry may be programmed to limit a scan to a frequency range within the gamma frequency band, such as 60-100 Hz. However, in some embodiments, control circuitry will cause the full spectrum of stimulation frequencies to be tested in one scan of stimulation frequencies. The frequency band to be scanned may be determined based on the condition being treated or may be based on the brain area targeted for stimulation. For example, a judgment may be made about which stimulation parameters to scan once it is understood what condition the patient suffers. If the patient suffers from Parkinson's disease, then control circuitry may automatically scan stimulation frequency ranges within the gamma frequency band, for example.

Based on the set 380 therapy parameters, a therapy may be delivered 390 for an extended period in a therapy phase using the therapy parameters. In various embodiments, scans are performed to vary stimulation parameters in establishing efficacious therapy parameters in a test phase (steps 310-380) and then the set 380 parameters are statically used for delivery 390 in the therapy phase.

Figure 4:
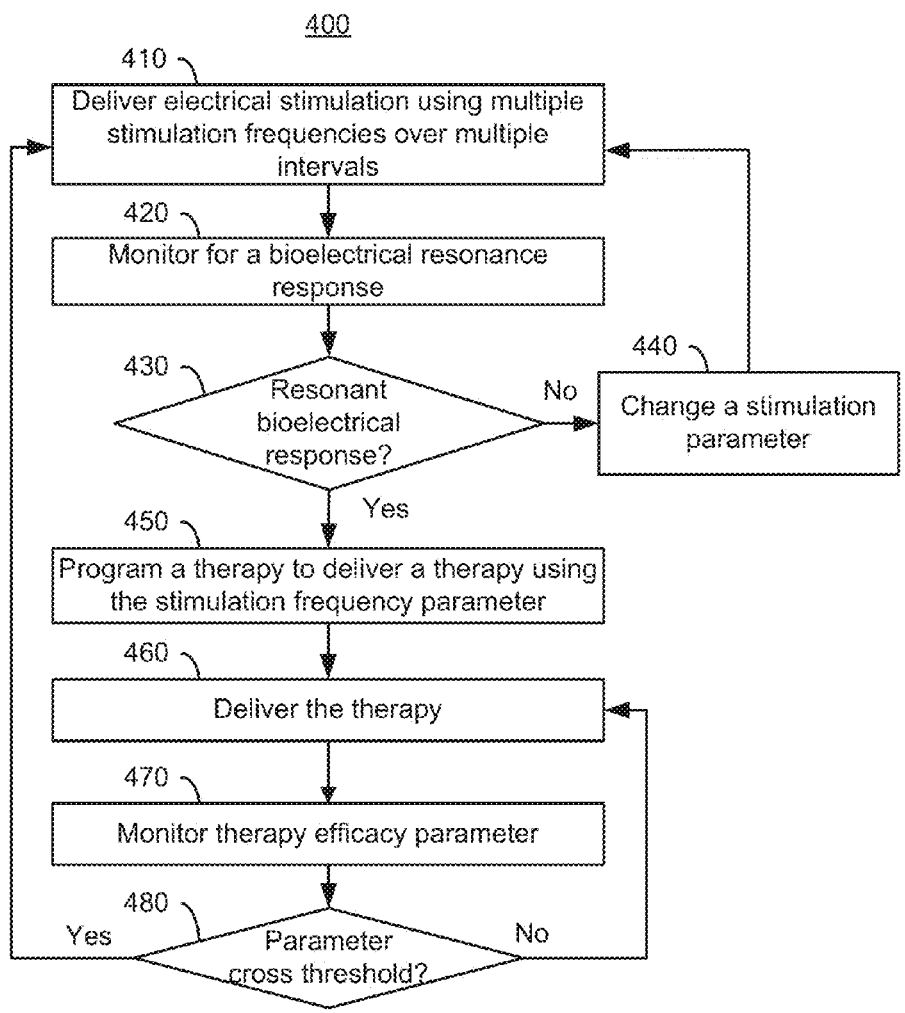
FIG. 4 is a flow diagram for adjusting stimulation parameters based on a bioelectrical resonance response.

FIG. 4 illustrates a method 400 for determining and resetting a stimulation frequency parameter over time. The method 400 includes delivering 410 electrical stimulation using multiple stimulation frequencies over multiple intervals, one stimulation frequency for each interval. The method 400 further includes monitoring 420 for a bioelectrical resonance response from the stimulation delivery 410. If the bioelectrical resonance response is not present 430, then a stimulation parameter can be changed 440 and another stimulation delivery 410 scan can be performed. The change 440 in the stimulation frequency parameter may relate to increasing a pulse voltage, increasing pulse width (or any other energy parameter), broadening or shifting a stimulation frequency range (e.g., raising the highest stimulation frequency of the range), changing the electrode combination used in stimulation, and/or changing some other aspect of stimulation. In this way, the method 400 can loop through delivering 410, monitoring 420, and changing 440 until a bioelectrical resonance response is recognized as being present 430.

A therapy can be programmed 450 (e.g., by transmitting the value to an implanted device or saving the stimulation frequency in memory of the implanted device) with the stimulation frequency parameter value that caused the bioelectrical resonance response and any other stimulation parameters, such as amplitude and pulse width. The therapy can then be delivered 460 using the stimulation frequency parameter value. During the course of therapy delivery 460, a parameter of therapy efficacy can be monitored 470. In various embodiments, the therapy efficacy parameter may indicate the presence or the amount of presence of the bioelectrical resonance response based on monitoring 470. As such, monitoring 470 be performed in a manner comparable to monitoring 420 with the further step of characterizing the presence of the bioelectrical resonant response. The therapy efficacy parameter may be the binary presence of the bioelectrical resonance response (e.g., it is present or is not present). The therapy efficacy parameter may characterize the degree of presence of the bioelectrical resonance response by determining the percent of time, minutes per hour, or episodes per hour or some other indicator of the presence of the bioelectrical resonance response over a time period. The therapy efficacy parameter may characterize the amount of presence of the bioelectrical resonance response by determining the strength of response, such as by analyzing the power spectrum of a sensed bioelectrical signal and determining the power level of the oscillatory response that is indicative of the bioelectrical resonance response (e.g., the power level at the frequency at which the brain area oscillates when exhibiting the bioelectrical resonance response, the power level proportional to the amount of presence past a certain power level that first indicates the presence). The therapy efficacy parameter may be based on the duration of the bioelectrical resonance response following temporary cessation of therapy. For example, the therapy may be periodically delivered 460 with the expectation that the bioelectrical resonance response continues for some time after each break (cessation) in stimulation. The therapy efficacy parameter may be based on the presence of regular stimulation peaks, the regularity of which the bioelectrical resonance response was determined to be present 430 (e.g., the number of peaks detected in monitoring 470 may be compared to a threshold number).

If the monitored 470 therapy efficacy parameter crosses a threshold 480, then the method 400 can return to the loop of delivering 410, monitoring 420, and changing 440 until a bioelectrical resonance response is again recognized as being present 430, which might be at a different stimulation frequency than before. If the monitored 470 therapy efficacy parameter does not cross the threshold 480, then the method 400 continues delivering 460 the therapy using the same stimulation frequency parameter, monitoring 470, and checking the efficacy threshold 480, all of which may be done concurrently or intermittently. The efficacy parameter threshold level can be a default level or it can be set as part of programming 450, for example. The efficacy parameter threshold can represent an unacceptable or non-optimal level of presence of the bioelectrical resonance response. For example, the efficacy parameter threshold can represent a level at which therapeutic benefits are believed to be diminished or otherwise non-optimal. The efficacy parameter threshold relates to the type of efficacy parameter, such that if the efficacy parameter is a duration of a bioelectrical resonance response, then the threshold relates to time, and if the efficacy parameter is a percentage of time of the presence of the bioelectrical resonance response, then the threshold relates to a percentage. In various embodiments where the efficacy parameter is a binary assessment of whether the bioelectrical resonance response is present, then the parameter threshold 480 can assess whether the resonant bioelectrical is present or not.

In some embodiments, the efficacy parameter is based on a user indication, where a user may provide an input based on observed symptoms (e.g., where the patient answers questions on a programmer as part of a periodic assessment of his or her symptoms). Additionally or alternatively, the efficacy parameter may relate to therapy side effects. The patient's perceived effectiveness of therapy (e.g., based on alleviation of symptoms) and/or the patient's perceived presence of side-effects can be quantized by the patient, such as by the patient rating one or both of therapy effectiveness and side-effects on a ten point scale. When the input indicates diminishing or unacceptable therapeutic benefits and/or increased or unacceptable side effects, the efficacy parameter threshold 480 is crossed and the method 400 can update the stimulation frequency and/or other stimulation parameters. The user indication may be binary, such as a yes or no answer to a query presented on a programmer asking whether the patient is experiencing symptoms or whether the therapy is ineffective. A "yes" indication can then fail the test of the efficacy parameter threshold 480 check while a "no" indication can continue therapy delivery 460. A bioelectrical resonance response can then be identified in a rescan and a therapy parameter reset. In this way, an update of a therapy parameter based on a bioelectrical resonance response can be triggered based on a user indication.

In some embodiments, a therapy efficacy parameter can be monitored 470 by sensing an objective measure of a condition which the therapy is attempting to address. For example, if the therapy is delivered 460 to treat a movement disorder (e.g., Parkinson's disease, essential tremor, dystonia), then an accelerometer signal can be sensed, the accelerometer placed externally or implanted to assess the motor condition. Patterns indicative of the movement disorder can be identified from the accelerometer signal (e.g., indicative of repetitive movement associated with Parkinson's disease or another condition). An efficacy parameter can be determined based on the identification of the pattern (e.g., the relative level, duration, intensity, or duration of the repetitive movement). If the pattern identification indicates symptoms of the motor condition, or an unacceptable level of the symptoms, then the efficacy parameter threshold 480 can be crossed and the method 400 can loop to scan again. A bioelectrical resonance response can then be identified in this rescan and a therapy parameter reset. In this way, an update of a therapy parameter based on a bioelectrical resonance response can be triggered based on a monitored signal.

It is noted that the method 400 of FIG. 4 may also relate to stimulation amplitude and/or other parameters of therapy delivery, such that the techniques for determining a stimulation parameter, tracking an efficacy parameter, and updating the stimulation parameter can also apply to determining a stimulation amplitude, pulse width, or other parameter. In various embodiments, an electrode on a lead may be advanced or retracted within the brain based on the presence or absence of the bioelectrical resonance response until an optimal electrode position is found that provides for evoking the bioelectrical resonance response while avoiding inappropriate stimulation (or alternatively, avoiding evoking the bioelectrical resonance response). An electrode or electrode combination for delivering therapy can also be selected or changed based on the presence or absence of the bioelectrical resonance response.

In various embodiments, the brain is continuously monitored for a bioelectrical resonance response during and shortly following therapy delivery. All signal data may be saved, or only selected portions corresponding to recognition of a bioelectrical resonance response may be saved, in some embodiments. Such chronic monitoring may be performed by a wearable external medical device and/or an implantable medical device. However, in some embodiments, monitoring brain areas and recognizing a bioelectrical resonance response may only occur in connection with specific testing periods, such as in initial programming of a device and with follow-up clinic visits. Various embodiments concern implanted control circuitry configured to carry out scanning, identification of a stimulation frequency that can evoke a bioelectrical resonance response, and setting of therapy parameters based on the identification as discussed herein. In some embodiments, control circuitry always monitors for a bioelectrical resonance response when stimulation is being delivered or has just been delivered in a therapy phase (e.g., such as in the case of FIG. 4 wherein the efficacy parameter relates to the presence of the bioelectrical resonance response) while in some other embodiments monitoring for the bioelectrical resonance response is performed only during discrete testing phases and not during all or any part of a therapy delivery phase.

A bioelectrical resonance response threshold can be developed for a particular patient in various embodiments. The bioelectrical resonance response threshold can be used to determine when the bioelectrical resonance response is present in a brain area, such as by a processor of control circuitry. The bioelectrical resonance response threshold can be particularly useful when a device is in a therapy delivery phase of operation (e.g., a frequency parameter is not being scanned as in the delivery 460 step of FIG. 4) and the bioelectrical resonance response would be expected. In such a case, a bioelectrical resonance response threshold can be based on the same parameter for which the bioelectrical resonance response was recognized in a scanning mode or test phase (e.g., corresponding to the delivering 410, monitoring 420, and changing 440 steps of FIG. 4). In various embodiments, when a bioelectrical resonance response is recognized as being present 430, a processor of control circuitry can analyze what parameter levels indicated the bioelectrical resonance response and set a threshold based on these parameters. For example, stimulation pulsed at 71 Hz may evoke the bioelectrical resonance response which may be characterized by a 73 Hz oscillation and may have been recognized based on a power spectral density (PSD) value of 58 microvolts squared per Hertz ($\mu v^2$/Hz) at 73 Hz. Accordingly, the threshold may be set at 58 $\mu v^2$/Hz for 73 Hz, or the power parameter may be set at a lower amount, such as four fifths or three fourths of the amount (e.g., at 46.4 $\mu v^2$/Hz or 43.5 $\mu v^2$/Hz, respectively). If the PSD for 73 Hz drops below the threshold, then the absence of the bioelectrical resonance response may be noted. A real-time drop of the power parameter below the threshold (e.g., the threshold 480 of FIG. 4) may immediately begin resetting the stimulation parameters, or a parameter may need to be below the threshold for a predetermined duration (e.g., 5 minutes) before the stimulation parameters are reset by scanning. Although the above example discusses the bioelectrical oscillatory response being characterized by a bioelectrical oscillation a few Hz away from the stimulation frequency, in some other cases larger differences between stimulation and bioelectrical oscillatory frequencies may be observed. For example, a bioelectrical oscillatory frequency may have a harmonic, multiple, or de-multiple relationship with the stimulation frequency. However, in some cases the stimulation and bioelectrical oscillatory frequencies will match, and matching will be a requirement for identifying the bioelectrical resonance response.

In various embodiments, the therapy is a continuous signal delivered using one, two, or more electrodes and the stimulation frequency parameter relates to modulation of a sinusoidal pattern of the signal. In some embodiments, discrete pulses are delivered, and the stimulation frequency parameter relates to the frequency with which individual pulses are delivered. In some embodiments, blanking in sensing and/or interruptions in delivery of an electrical therapy can be used to allow sensing of bioelectrical signals generally concurrent electrical stimulation.

The targeted area, as used herein, refers to the neurological area that exhibits a bioelectrical resonance response to stimulation of a particular frequency. In various embodiments, electrical therapy is delivered directly to the targeted area to produce the bioelectrical resonance response by locating an electrode within the targeted area and using the electrode as a cathode or anode during delivery of electrical energy. In some cases it may be preferable to directly stimulate an associated brain area (e.g., remote from the targeted area) to evoke the bioelectrical resonance response in the targeted area. In such cases, the targeted area may be electrically "down stream" from the associated brain area to which the electrical therapy is directly delivered, such that it is more effective and/or safer to electrically treat the targeted area remotely than directly. Stimulation delivered to the associated portion of the brain, rather than directly to the targeted portion, may have broader outputs to larger areas of the brain outside and including the targeted portion of the brain, in various embodiments, the subthalamic nucleus may be stimulated in a Parkinson's disease patient, although other areas are contemplated for this and other disorders, such as the basal ganglia, cerebellum, thalamus, globus pallidus interna (GPi), globus pallidus external (GPe), cortex, substantia nigra (both compacta (SNc) and reticulata (SNr)), among other areas. Some targets and/or directly stimulated areas may be outside of the brain, such as peripheral nerves or specifically the vagus nerve. In the case of Alzheimer's disease patients, various therapies may be an electrical signal delivered to the thalamus or hippocampus of a patient at around 1-200 Hz. and at 0.5-10 volts with a pulse width of 50-200 microseconds, amongst other targets and parameters. Various conditions and neurological disorders tier which stimulation parameters can be set as discussed herein include movement disorders, sleep disorders, seizure disorders, eating disorders, dementia. Huntington's disease, autism, addiction, obesity, depression, autonomic dysfunction, hypertension, and heart failure, among others.

Various embodiments can include use of fMRI and other functional brain imaging techniques. Brain imaging can be used to determine which brain areas should be activating and to guide therapy. fMRI can map brain activity to a 2D or 3D plot (e.g., on a display) allowing activated brain areas to be identified, usually indicated by being colored or otherwise highlighted. Concurrent sensing of a bioelectrical resonance response and a spatial activation indication of an fMRI display may be used to corroborate bioelectrical response results, help guide lead placement, and facilitate electrode selection (e.g., advancing a lead to a highlighted area and/or by selecting one or more electrodes proximate the highlighted area). While fMRI is used as an exemplar in this disclosure, all other types of neural imaging are contemplated to be used in the same way, including magneto encephalography and positron emission tomography.

The various techniques discussed herein may be performed, in whole or in part, by control circuitry. For example, control circuitry of a medical device may carry out each of the steps of FIGS. 1-4. In this way, the techniques discussed in association with FIGS. 1-4 are useable together and do not necessarily present exclusive features of the embodiments presented herein. The features of the present disclosure can be selectively used in a single embodiment, even if the features are separately discussed (e.g., select steps from each FIGS. 1-4 can be chosen for use in an implantable medical device to set a stimulation frequency parameter and deliver a therapy). Control circuitry is further discussed in association with FIGS. 5 and 6.

Figure 5:
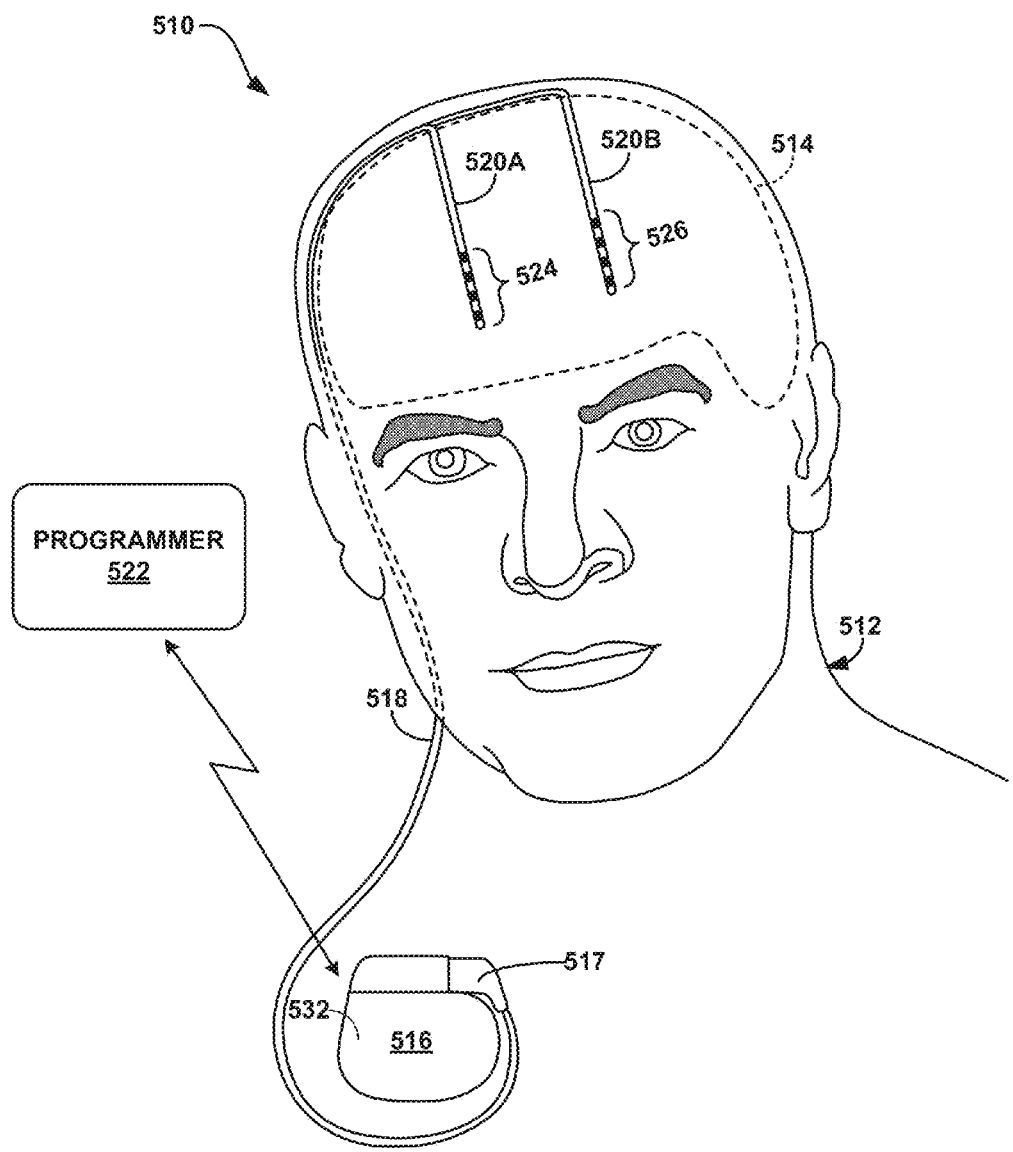
FIG. 5 is a conceptual diagram illustrating an example therapy system that delivers therapy to a patient to manage a disorder of the patient.

FIG. 5 is a conceptual diagram illustrating an example therapy system 510 that monitors a brain condition and/or delivers therapy to patient 512 to manage the brain condition of patient 512. System 510 includes implantable medical device (IMD) 516, lead extension 518, one or more leads 520A and 520B (collectively "leads 520") with respective sets of electrodes 524, 526, and medical device programmer 522. In various embodiments, IMD 516 includes a module as part of control circuitry that senses electrical brain signals and identifies brain activity and conditions via the electrodes 524, 526 of leads 520A and 520B, respectively.

System 510 may monitor one or more bioelectrical brain signals of patient 512. For example, IMD 516 may include a sensing module (e.g., sensing module 544 of FIG. 6) that senses bioelectrical brain signals within one or more regions of brain 514. In the embodiment shown in FIG. 5, the signals may be sensed by electrodes 524, 526 and conducted to the sensing module within IMD 516 via conductors within the respective lead 520A, 520B. As described in further detail below, in some examples, control circuitry of IMD 516 or another device (e.g., programmer 522) monitors the bioelectrical signals within brain 514 of patient 512 with a processor to recognize a bioelectrical resonance response, set one or more stimulation parameters, and/or perform the other functions referenced herein including those of FIGS. 1-4. Control circuitry of MID 516 or another device (e.g., programmer 522) may control delivery of electrical therapy to brain 514 with a processor based on the which stimulation frequency of a scan provoked a bioelectrical resonance response in a manner that treats a brain condition of patient 512.

In some examples, the sensing module of IMD 516 may receive the bioelectrical signals from electrodes 524, 526 or other electrodes positioned to monitor bioelectrical brain signals of patient 512 (e.g., if housing 532 of IMD 516 is implanted in or proximate brain 514, then an electrode of housing 532 may be used to sense bioelectrical brain signals and/or deliver stimulation to brain 514). Electrodes 524, 526 may also be used to deliver electrical stimulation from the therapy module to target sites within brain 514 as well as to sense brain signals within brain 514. However, IMD 516 can also use separate sensing electrodes to sense the bioelectrical brain signals. In some examples, the sensing module of IMD 516 may sense bioelectrical brain signals via one or more of the electrodes 524, 526 that are also used to deliver electrical stimulation to brain 514. In other examples, one or more of electrodes 524, 526 may be used to sense bioelectrical brain signals while one or more different electrodes 524, 526 may be used to deliver electrical stimulation.

The bioelectrical brain signals monitored by IMD 516 may reflect changes in electrical current produced by the sum of electrical potential differences across brain tissue. Examples of the monitored bioelectrical signals include, but are not limited to, an EEG signal, a ECoG signal, a LFP signal sensed from within one or more regions of brain 514, and/or action potentials from single cells within the brain 514 or outside of brain. These and other signals can be used to perform the various functions referenced herein, including recognition of a bioelectrical resonance response.

Therapy system 510 may be implemented to provide chronic stimulation therapy to patient 512 over the course of several months or years. However, system 510 may also be employed on a trial basis to evaluate therapy before committing to full implantation. If implemented temporarily, some components of system 510 may not be implanted within patient 512. For example, patient 512 may be fitted with an external medical device, such as a trial stimulator, rather than IMD 516. The trial simulation may have essentially all of the control circuitry of the Imp 516 and may be configured to perform any of the functions disclosed herein in the same manner as IMD 516. The external medical device may be coupled to percutaneous leads or to implanted leads via a percutaneous extension. If the trial stimulator indicates DBS system 510 provides effective treatment to patient 512, the clinician may implant a chronic stimulator within patient 512 for relatively long-term treatment. In such cases, the monitoring functions discussed herein are performed by external sensors and circuitry while stimulation functions are performed by implanted circuitry (although in some embodiments the IMD 516 still has circuitry for sensing and setting stimulation parameters based on a bioelectrical resonance response as discussed herein). External monitoring can be performed by sensing one or more EEG signals with electrodes placed on the head of a patient. The external monitoring can sense an EEG and analyze the signal as discussed herein for identifying a bioelectrical resonance response.

As discussed herein, the monitored brain signals of patient 512 may be used to recognize a bioelectrical resonance response of brain 514. Metrics that can be used to detect network activation and further recognize bioelectrical resonance response episodes include time domain characteristics (e.g., an amplitude or phase) or frequency domain characteristics (e.g., a power level in one or more frequency bands) of the brain signals sensed by IMD 516 within one or more regions of brain 514. For example, the characteristic of the brain signals may include an absolute amplitude value or a root mean square amplitude value. In addition, the amplitude value may comprise an average, peak, mean, spike, or instantaneous amplitude value over a period of time or a maximum amplitude or an amplitude in a particular percentile of the maximum (e.g., an amplitude value that represents 95% of the maximum amplitude value). The timing of signal features may be determined to recognize any oscillatory patterns in the sensed signal, which may be indicative of a bioelectrical resonance response.

In various embodiments, the characteristic of the brain signal may include the frequency, amplitude, and phase of the bioelectrical brain signal(s) sensed within one or more regions of brain 514 of patient 512. The frequency, amplitude, and phase of the bioelectrical brain signal may indicate the oscillations in the brain signal and be used to determine the degree to which a brain area is exhibiting an oscillatory pattern indicative of a bioelectrical resonance response. The oscillations in the sensed bioelectrical brain signals may represent the rhythmic or repetitive neural activity in brain 514 when a particular network of an area is activated in response to stimulation of a particular frequency. The neural oscillations may be determined based on one or more frequency domain characteristics of the bioelectrical brain signal.

In various embodiments, IMD 516 may deliver therapy to any suitable portion of brain 514 that exhibits a bioelectrical resonance response, although neural circuits that feed into and/or are wholly outside of the brain can also be monitored and stimulated as discussed herein on the basis of evoking a bioelectrical resonance response. In some embodiments, system 510 may deliver therapy to patient 512 to manage a neurological disorder of patient 512. For example, system 510 may provide therapy to correct a brain disorder, injury, and/or manage symptoms of a neurodegenerative brain condition. Patient 512 ordinarily will be a human patient. In some cases, however, system 510 and the techniques disclosed herein may be applied to other mammalian non-human or non-mammalian subjects. While examples of the disclosure are described with regard to tracking and treatment of a cognitive disorder such as Parkinson's disease, in other examples, system 510 may set stimulation parameters and deliver therapy to manage symptoms of other patient conditions.

IMD 516 may include a module that includes a stimulation generator that generates and delivers electrical stimulation therapy to one or more regions of brain 514 of patient 512 via the electrodes 524, 526 of leads 520A and 520B, respectively. In the example shown in FIG. 5, system 510 may be referred to as deep brain stimulation system because IMD 516 may provide electrical stimulation therapy directly to tissue within brain 514, e.g., a tissue site under the dura mater of brain 514. In other embodiments, leads 520 may be positioned to sense brain activity and/or deliver therapy to a surface of brain 514, such as the cortical surface of brain 514, or the spinal cord.

In the example shown in FIG. 5, IMD 516 may be implanted within a subcutaneous pocket below the clavicle of patient 512. In other embodiments, IMD 516 may be implanted within other regions of patient 512, such as a subcutaneous pocket in the abdomen or buttocks of patient 512, proximate the cranium, or on/in the cranium of patient 512. Implanted lead extension 518 is coupled to IMD 516 via a connector block (also referred to as a header), which may include, for example, electrical contacts that electrically couple to respective electrical contacts on lead extension 518. The electrical contacts electrically couple the electrodes 524, 526 carried by leads 520 to IMD 516. Lead extension 518 traverses from the implant site of IMD 516 within a chest cavity of patient 512, along the neck of patient 512 and through the cranium of patient 512 to access brain 514. Generally, IMD 516 is constructed of a biocompatible material that resists corrosion and degradation from bodily fluids. IMD 516 may comprise a hermetic housing 532 to substantially enclose control circuitry, such as a processor, memory, and signal processing components. In various embodiments, IMD 516 may be implanted only in the head of the patient (e.g., under the scalp) and not in the chest and neck regions.

Electrical stimulation may be delivered to one or more regions of brain 514, which may be selected based on many factors, such as the type of patient condition for which system 510 is implemented to manage and which brain areas exhibit a bioelectrical resonance response. In some examples, leads 520 may be implanted within the right and left hemispheres of brain 514 (e.g., as illustrated in FIG. 5) while, in other cases, only one, or both of leads 520, may be implanted within one of the right or left hemispheres. Other implant sites for leads 520 and IMD 516 are contemplated. For example, IMD 516 may be implanted on or within cranium. In addition, in some examples, leads 520 may be coupled to a single lead that is implanted within one hemisphere of brain 514 or implanted through both right and left hemispheres of brain 514.

Leads 520 may be positioned to deliver electrical stimulation to one or more target tissue sites within brain 514 to manage patient symptoms associated with a disorder of patient 512. Targeted tissues may be the tissues that exhibit a bioelectrical resonance response. Leads 520 may be implanted to position electrodes 524, 526 at desired locations of brain 514 through respective holes in cranium. Leads 520 may be placed at any location within brain 514 such that electrodes 524, 526 are capable of providing electrical stimulation to target tissue sites within brain 514 during treatment. In some embodiments, leads may be placed such that electrodes 524, 526 directly contact or are otherwise proximate targeted tissue of a particular brain area.

In the example shown in FIG. 5, electrodes 524, 526 of leads 520 are shown as ring electrodes. Ring electrodes may be relatively easy to program and are typically capable of sensing and/or delivering an electrical field to any tissue adjacent to leads 520 (e.g., in all directions away from an outer perimeter of leads 520). In other examples, electrodes 524, 526 of leads 520 may have different configurations. For example, electrodes 524, 526 of leads 520 may have a complex electrode array geometry that is capable of producing shaped electrical fields. The complex electrode array geometry may include multiple electrodes (e.g., partial ring or segmented electrodes) around the perimeter of each lead 520, rather than a ring electrode. In this manner, electrical brain sensing and/or electrical stimulation may be associated with a specific direction from leads 520 (e.g., in a direction less than around the entire outer perimeter of leads 520) to enhance directional sensing and/or therapy efficacy and reduce possible adverse side effects from stimulating a large volume of tissue in the case of stimulation. As such, electrodes can be positioned to stimulate targeted tissue and avoid stimulating non-targeted tissue.

In some embodiments, outer housing 532 of IMD 516 may include one or more stimulation and/or sensing electrodes. For example, housing 532 can comprise an electrically conductive material that is exposed to tissue of patient 512 when IMD 516 is implanted in patient 512, or an electrode can be attached to housing 532. In stimulation, the housing 532 electrode can serve as an anode and an electrode in the brain can serve as the cathode, for example. In some examples, leads 520 may have shapes other than elongated cylinders as shown in FIG. 5. For example, leads 520 may be paddle leads, spherical leads, bendable leads, or any other type of shape effective in treating patient 512.

Stimulation generator 542, under the control of processor 540, generates stimulation signals for delivery to patient 512 via selected combinations of electrodes 524, 526. Stimulation generator 542 may include one or more capacitors and/or other electrical energy management components for temporarily storing electrical energy from power source 550 before discharge via selected combinations of electrodes 524, 526. Processor 540 as part of control circuitry controls stimulation generator 542 according to stimulation programs 552 stored in memory 541 to apply particular stimulation parameter values specified by one or more programs, such as amplitude, pulse width, and pulse rate, in accordance with the various embodiments of this disclosure. In some examples, stimulation generator 542 generates and delivers stimulation signals to one or more target portions of brain 514 via a select combination of electrodes 524, 526.

Stimulation generator 542 may be configured to generate various stimulation profiles and parameter ranges. For example, the stimulation generator of IMD 516 may be configured to generate and deliver discrete pulses to patient 512. However, in other examples, the stimulation generator of IMD 516 may be configured to generate and deliver a continuous wave signal, e.g., a sine wave or triangle wave. In either case, a signal generator within IMD 516 may generate the electrical stimulation therapy for DBS according to a therapy program that is selected at that given time in therapy. In examples in which MID 516 delivers electrical stimulation in the form of stimulation pulses, a therapy program may include a set of therapy parameter values, such as stimulation frequency which concerns the rate at which pulses are delivered, pulse width, and a current or voltage amplitude of the pulses.

Stimulation generator 542 may be configured to generate various stimulation parameter ranges. For example, therapy may be delivered at various voltages, which can vary between approximately 0.1 volts and approximately 50 volts, and between approximately 0.5 volts and approximately 20 volts, at approximately 5 volts, although other ranges and values are contemplated. Various current amplitudes are contemplated. Current amplitude may be defined as the biological load in which the voltage is delivered. In a current-controlled system, the current amplitude, assuming a lower level impedance of approximately 500 ohms, may be between approximately 0.2 milliamps to approximately 100 milliamps, such as between approximately 1 milliamps and approximately 40 milliamps, or approximately 10 milliamps. However, in some examples, the impedance may range between about 200 ohms and about 2 kilo ohms. Various pulse widths are contemplated, including but not limited to between approximately 10 microseconds and approximately 5000 microseconds, such as between approximately 100 microseconds and approximately 1000 microseconds, or between approximately 180 microseconds and approximately 450 microseconds.

Leads 520 may be implanted within a desired location of brain 514 via any suitable technique, such as through one or more burr holes in a skull of patient 512. Leads 520 may be placed at any location within brain 514 such that electrodes 524, 526 of leads 520 are capable of sensing electrical activity of the brain areas of (e.g., a bioelectrical resonance response), and/or providing electrical stimulation to, targeted tissue for treatment.

In some examples, a processor of system 510 (e.g., a processor of control circuitry of programmer 522 and/or IMD 516) controls delivery of electrical stimulation through stimulation generator 542 by activating electrical stimulation, deactivating electrical stimulation, increasing stimulation frequency, decreasing stimulation frequency, increasing the intensity of electrical stimulation, or decreasing the intensity of electrical stimulation delivered to brain 514 to scan and titrate electrical stimulation therapy. Therapy can be started, stopped, and/or changed by processor 540 in any manner and based on any parameter or finding as discussed herein.

System 510 may also store a plurality of stimulation programs (e.g., a set of electrical stimulation parameter values that are established to produce a bioelectrical resonance response). A processor as part of control circuitry of IMD 516 or programmer 522 may select a stored stimulation program that defines electrical stimulation parameter values for delivery of electrical stimulation to brain 514 based on a bioelectrical resonance response. Where IMD 516 delivers electrical stimulation in the form of electrical pulses, for example, the stimulation therapy may be characterized by selected pulse parameters, such as pulse amplitude, pulse rate, and pulse width. In addition, if different electrodes are available fir delivery of stimulation, the therapy may be further characterized by different electrode combinations, which can include selected electrodes and their respective polarities.

External programmer 522 wirelessly communicates with IMD 516 as needed to provide or retrieve information. For example, external programmer 522 may receive sensed data and/or information regarding a bioelectrical resonance response from IMD 516, as well as send therapy program information to IMD 516. Programmer 522 is an external computing device that the user, e.g., the clinician and/or patient 512, may use to communicate with IMD 516. For example, programmer 522 may be a clinician programmer that the clinician uses to communicate with IMD 516 and program one or more therapy programs for IMD 516. Additionally or alternatively, programmer 522 may be a patient programmer that allows patient 512 to input information (e.g., a self evaluated assessment), select programs, and/or view and modify therapy parameters.

Programmer 522 may be a hand-held computing device with a display viewable by the user and an interface for providing input to programmer 522 (i.e., a user input mechanism). For example, programmer 522 may include a small display screen (e.g., a liquid crystal display (LCD) or a light emitting diode (LED) display) that presents information to the user, such as power spectrum. Programmer 522 may include a touch screen display, keypad, buttons, a peripheral pointing device or another input mechanism that allows the user to navigate though the user interface of programmer 522 and provide input. The screen (not shown) of programmer 522 may be a touch screen that allows the user to provide input directly to the user interface shown on the display. The user may use a stylus or their finger to provide input to the display.

In other examples, programmer 522 may be a larger workstation or a separate application within another multi-function device, rather than a dedicated computing device. For example, the multi-function device may be a notebook computer, tablet computer, workstation, server, cellular phone, personal digital assistant or another computing device.

When programmer 522 is configured for use by the clinician, programmer 522 may be used to transmit initial programming information to IMD 516. This initial information may include hardware information, such as the type of leads 520, the arrangement of electrodes 524, 526 on leads 520, the position of leads 520 within brain 514, initial programs defining therapy parameter values and stimulation parameter ranges to scan, and any other information that may be useful for programming into IMD 516. Programmer 522 may also be capable of completing functional tests (e.g., measuring the impedance of electrodes 524, 526 of leads 520). Programmer 522 may include control circuitry configured to perform any of the steps discussed herein, such as those of FIG. 1-4. For example, in the case that an implantable medical device is not used in a test phase and a programmer 522 is used in the test phase to connect to leads 520, scan a stimulation frequency range, identify which one stimulation frequency produces a bioelectrical resonance response in a brain area, and program a device (e.g., IMD 516) to deliver therapy using the one stimulation frequency in a therapy phase. Control circuitry may be distributed between the programmer 522 and the IMD 516 to carry out the functions disclosed herein.

The clinician may store therapy programs within IMD 516 with the aid of programmer 522. During a programming session, the clinician may determine one or more stimulation programs that may effectively bring about a therapeutic outcome that treats a brain condition, such as facilitating a bioelectrical resonance response from one or more brain areas. For example, the clinician may select one or more electrode combinations with which stimulation is delivered to brain 514 to produce a bioelectrical resonance response. During the programming session, the clinician may evaluate the efficacy of the one or more electrode combinations based on one or more findings of an fMRI, patient self reporting, LFP, EEG, or some other parameters associated with a bioelectrical resonance response of brain areas of the patient 512. In some examples, programmer 522 may assist the clinician in the creation/identification of stimulation programs by providing a methodical system for identifying potentially effective stimulation parameter values. In some examples, the control circuitry of programmer 522 may calculate and display one or more therapy metrics for evaluating and comparing therapy programs available for delivery from IMD 516 to patient. Programmer 522 may present an indication of a bioelectrical resonance response or other information in any suitable manner. In some examples, programmer 522 may display a time domain plot of an evoked bioelectrical brain signal and indicate a suspected signature of a bioelectrical resonance response. In other examples, programmer 522 may display a table that provides the relative gamma frequency band (or other frequency band of interest) power level associated with each stimulation interval.

Programmer 522 may also provide an indication to patient 512 when therapy is being delivered which may aid the assessment of therapy efficacy. For example, upon seeing that therapy is being delivered the patient may evaluate whether he or she has cessation of symptoms (e.g., fewer tremors or other symptom of a movement disorder) by answering questions presented on the programmer 522.

Whether programmer 522 is configured for clinician or patient use, programmer 522 may be configured to communicate with IMD 516 and, optionally, another computing device, via wireless communication. Programmer 522, for example, may communicate via wireless communication with IMD 516 using radio frequency (RF) telemetry techniques. Programmer 522 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 522 may also communicate with other programming or computing devices via exchange of removable media, such as magnetic or optical disks, memory cards or memory sticks. Further, programmer 522 may communicate with IMD 516 and another programmer via remote telemetry techniques known in the art, communicating via a local area network (LAN), wide area network (WAN), public switched telephone network (PSTN), or cellular telephone network, for example.

FIG. 5 is a functional block diagram illustrating components of IMD 516. In the example shown in FIG. 5, IMD 516 includes processor 540, memory 541, stimulation generator 542, sensing module 544, which can be control circuitry as means for performing functions as described herein (e.g., delivering electrical stimulation over a frequency range, sensing signals, recognizing a bioelectrical resonance response, and setting one or more therapy stimulation parameters based on which one stimulation frequency caused the bioelectrical resonance response). Memory 541 may include any volatile or non-volatile media, such as a random access memory (RAM), read only memory (ROM), non-volatile RAM (NVRAM), electrically erasable programmable ROM (EEPROM), flash memory, and the like. Memory 541 may store computer-readable instructions as part of operating instructions 556 that, when executed by processor 540, cause IMD 516 to perform various functions described herein.

The steps, procedures, techniques, etc. referenced herein may be carried out by, for example, software instructions, such as those used to define a software or computer program. The computer-readable medium may store instructions. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) programmable to cause a processor to perform the actions described herein as part of control circuitry.

As another technique that can be implemented by a processor 540 as part of control circuitry for recognizing a bioelectrical resonance response, memory 541 may store portions of bioelectrical brain signals (e.g., waveforms or specific values of signal characteristics) previously sensed within brain 514 of patient that corresponds to a bioelectrical resonance response. In some examples, the stored bioelectrical brain signals can be used as a template to determine whether a particular sensed bioelectrical brain signal is indicative of a bioelectrical resonance response. As an example of a signal processing technique that control circuitry may employ to determine whether the bioelectrical brain signal includes the biomarker associated with a bioelectrical resonance response, processor 540 may analyze the bioelectrical brain signal with feature correlation, temporal correlation, or frequency correlation with a template signal, or combinations thereof. As another example, a slope of the amplitude of the bioelectrical brain signal over time or timing between inflection points or other critical points in the pattern of the amplitude of the bioelectrical brain signal over time may be compared to trend information stored in memory. A correlation between the inflection points in the amplitude waveform of the bioelectrical brain signal or other critical points and a template may indicate the bioelectrical brain signal includes the biomarker indicative of the bioelectrical resonance response. However, various embodiments may function in alternative manners.

As another technique for detection of a bioelectrical resonance response, processor 540 as part of control circuitry may perform temporal correlation by sampling the waveform generated by a sensed bioelectrical brain signal with a sliding window and comparing the waveform with a template waveform stored in memory that is associated with a previously confirmed bioelectrical resonance response. For example, processor 540 may perform a correlation analysis by moving a window along a digitized plot of the amplitude waveform of a sensed bioelectrical brain signal at regular intervals, such as between about one millisecond to about ten millisecond intervals, to define a sample of the bioelectrical brain signal. The sample window is slid along the plot until a correlation is detected between the waveform of the template and the waveform of the sample of the brain signal defined by the window. By moving the window at regular time intervals, multiple sample periods are defined. The correlation may be detected by, for example, matching multiple points between the template waveform and the waveform of the plot of the sensed bioelectrical brain signal over time, or by applying any suitable mathematical correlation algorithm between the sample in the sampling window and a corresponding set of samples stored in the template waveform.

As shown, the set of electrodes 524 of lead 520A includes electrodes 524A, 524B, 524C, and 524D and the set of electrodes 526 of lead 520B includes electrodes 526A, 526B, 526C, and 526D. Processor 540 may control switch module 546 to apply the stimulation signals generated by stimulation generator 542 to selected combinations of electrodes 524, 526. In particular, switch module 546 may couple stimulation signals to selected conductors within leads 520, which, in turn, deliver the stimulation signals across selected electrodes 524, 526. Switch module 546 may be a switch array, switch matrix, multiplexer, or any other type of switching module configured to selectively couple stimulation energy to selected electrodes 524, 526 and to selectively sense bioelectrical brain signals with selected electrodes 524, 526. Hence, stimulation generator 542 is coupled to electrodes 524, 526 via switch module 546 and conductors within leads 520. In some examples, however, IMD 516 does not include switch module 546.

Sensing module 544 is configured to sense bioelectrical brain signals of patient 512 via a selected subset of electrodes 524, 526, or with one or more electrodes 524, 526 and at least a portion of a conductive outer housing 532 of IMD 516, an electrode on an outer housing of IMD 516, or another reference. Processor 540 may control switch module 546 to electrically connect sensing module 544 to selected electrodes 524, 526. In this way, sensing module 544 may selectively sense bioelectrical brain signals with different combinations of electrodes 524, 526 (and/or a reference other than an electrode 524, 526).

Sensing of brain signals and detecting events (e.g., such as detecting a bioelectrical resonance response as a biomarker) can be implemented in view of commonly assigned U.S. Provisional Patent Application No. 61/527,387, filed on Aug. 25, 2011, by Carlson et al., titled METHOD AND APPARATUS FOR DETECTING A BIOMARKER IN THE PRESENCE OF ELECTRICAL STIMULATION, which is incorporated by reference herein in its entirety. Furthermore, setting algorithms for event detection, such a bioelectrical resonance response, can be implemented in view of commonly assigned U.S. Pat. App. No. 2010/0280335 to Carlson et al., which is entitled "PATIENT STATE DETECTION BASED ON SUPERVISED MACHINE LEARNING BASED ALGORITHM" filed Nov. 4, 2010; and U.S. Pat. App. No. 2010/0280334 to Carlson et al., which is entitled "PATIENT STATE DETECTION BASED ON SUPPORT VECTOR MACHINE BASED ALGORITHM" filed Nov. 4, 2010, which are incorporated herein by reference in their entireties.

Processor 540 may determine a relative gamma band power of each sensed bioelectrical brain signal. In some cases, sensing module 544 may include circuitry to tune to and extract a power level of a particular frequency band of a sensed bioelectrical brain signal. Thus, the power level of a particular frequency band of a sensed bioelectrical signal may be extracted prior to digitization of the signal by processor 540. By tuning to and extracting the power level of a particular frequency band before the signal is digitized, it may be possible to run frequency domain analysis algorithms at a relatively slower rate compared to systems that do not include a circuit to extract a power level of a particular frequency band of a sensed bioelectrical brain signal prior to digitization of the signal. In some examples, sensing module 544 may include more than one channel to monitor simultaneous activity in different frequency bands, i.e., to extract the power level of more than one frequency band of a sensed bioelectrical brain signal.

Processor 540 may determine and compare absolute or relative values of monitored parameters, such as frequency domain characteristics, to recognize a bioelectrical resonance response. A frequency domain characteristic of the bioelectrical signal may include, for example, a power level (i.e. energy) within one or more frequency bands of the bioelectrical signal, a ratio of the power level in two or more frequency bands, a correlation in change of power between two or more frequency bands, a pattern in the power level of one or more frequency bands over time, and the like.

Clinician, processor 540 of IMD 516, or a processor of another device as part of control circuitry, such as programmer 522, may determine the one or more biomarkers indicative of bioelectrical resonance response based on the bioelectrical signal(s). The biomarkers may be selected by the clinician or automatically by a processor of control circuitry, and may be selected as the signal characteristics that distinguish the bioelectrical resonance response of a brain area from a bioelectrical brain signal sensed when the bioelectrical resonance response is not present. The biomarker can then serve as a bioelectrical resonance response threshold or other indicator for subsequent detection of the bioelectrical resonance response.

Processor 540 as part of control circuitry may monitor bioelectrical brain signals sensed by sensing module 544 in any suitable manner in order to recognize a bioelectrical resonance response. For example, sensing module 544 may directly sense one or more bioelectrical brain signals, e.g., a LFP, via one or more of electrodes 524, 526. In some examples, processor 540 may compare one or more characteristics (e.g., amplitude, frequency, and/or power level) of the bioelectrical brain signal sensed (before, during, and/or after stimulation) in association with delivery of electrical stimulation at one frequency to other bioelectrical brain signals sensed in connection with delivery of electrical stimulation delivered at other frequencies to recognize a single stimulation frequency of a frequency range that evokes the bioelectrical resonance response. Memory 541 may store information related to signals sensed and power spectrums and other characteristics that can indicate a bioelectrical resonance response.

In various embodiments, system 510 may include one or more external electrodes positioned on the outer surface of the cranium of patient 512 that can sense and generate a bioelectrical brain signal, e.g., an EEG signal, that can be used to recognize a bioelectrical resonance response.

Although sensing module 544 is incorporated into a common housing 532 with stimulation generator 542 and processor 540, in other examples, sensing module 544 is in a physically separate outer housing from outer housing 532 of IMD 516 and communicates with processor 540 via wired or wireless communication techniques.

Telemetry module 548 under the control of processor 540 supports wireless communication between IMD 516 and an external programmer 522 or another computing device. Processor 540 of IMD 516 may receive, as updates to sensing and/or stimulation programs, values for stimulation parameters such as amplitude and electrode combination information from programmer 522 via telemetry module 548. The updates to the stimulation, sensing, or other programs may be stored within stimulation programs 552 of memory 541. Telemetry module 548 in IMD 516, as well as telemetry modules in other devices and systems described herein, such as programmer 522, may accomplish communication by RF communication techniques. In addition, telemetry module 548 may communicate with external medical device programmer 522 via proximal inductive interaction of IMD 516 with programmer 522 or other external device. Accordingly, telemetry module 548 may send information to external programmer 522 on a continuous basis, at periodic intervals, or upon request from IMD 516 or programmer 522. For example, processor 540 may transmit sensed signals and/or information relating to recognition of a bioelectrical resonance response to programmer 522 via telemetry module 548.

Power source 550 delivers operating power to various components of IMD 516. Power source 550 may include a small rechargeable or non-rechargeable battery and a power generation circuit to produce the operating power. Recharging may be accomplished through proximal inductive interaction between an external charger and an inductive charging coil within IMD 516. In various embodiments, traditional batteries may be used, such as a nonrechargeable primary cell battery.

Figure 6:
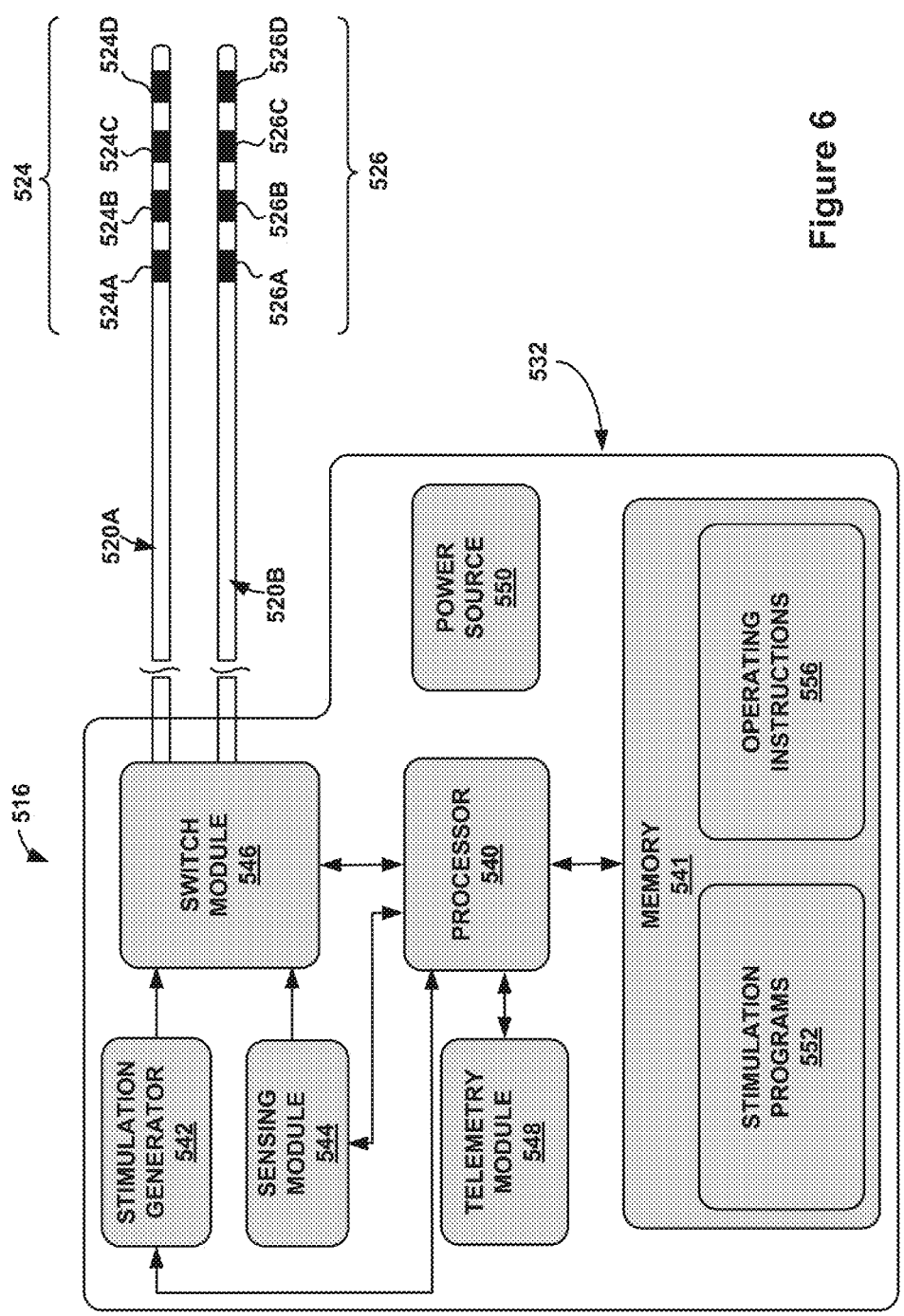
FIG. 6 is a functional block diagram illustrating control circuitry of a medical device.

Although the control circuitry of FIG. 6 is generally illustrated and described in terms of an implantable medical device, the control circuitry could alternatively be embodied in an at least partially external device and, depending on the therapy and/or circuitry configuration, may be wholly external.

The techniques described in this disclosure, including those of FIGS. 1-6 and those attributed to programmer, IMD, processor, and/or control circuitry, or various constituent components, may be implemented wholly or at least in part, in hardware, software, firmware or any combination thereof. A processor, as used herein, refers to any number and/or combination of a microprocessor, a digital signal processor (DSP), an application specific integrated circuit (ASIC), a field-programmable gate array (FPGA), microcontroller, discrete logic circuitry, processing chip, gate arrays, and/or any other equivalent integrated or discrete logic circuitry. "Control circuitry" as used herein refers to at least one of the foregoing logic circuitry as a processor, alone or in combination with other circuitry, such as memory or other physical medium for storing instructions, as needed to carry about specified functions (e.g., a processor and memory having stored program instructions executable by the processor for causing an implanted medical device to vary stimulation frequency to identify which one stimulation frequency produces a bioelectrical resonance response and then use the one stimulation frequency for therapy delivery). The functions referenced herein and those functions of FIGS. 1-6, may be embodied as firmware, hardware, software or any combination thereof as part of control circuitry specifically configured (e.g., with programming) to carry out those functions, such as in means for performing the functions referenced herein. The steps described herein may be performed by a single processing component or multiple processing components, the latter of which may be distributed amongst different coordinating devices (e.g., an and an external programmer). In this way, control circuitry may be distributed between multiple devices, including an implantable medical device and an external medical device in various systems. In addition, any of the described units, modules, or components may be implemented together or separately as discrete but interoperable logic devices of control circuitry. Depiction of different features as modules or units is intended to highlight different functional aspects and does not necessarily imply that such modules or units must be realized by separate hardware or software components and/or by a single device. Rather, functionality associated with one or more module or units, as part of control circuitry, may be performed by separate hardware or software components, or integrated within common or separate hardware or software components of the control circuitry.

When implemented in software, the functionality ascribed to the systems, devices and control circuitry described in this disclosure may be embodied as instructions on a physically embodied computer-readable medium such as RAM, ROM, NVRAM, EEPROM, FLASH memory, magnetic data storage media, optical data storage media, or the like, the medium being physically embodied in that it is not a carrier wave, as part of control circuitry. The instructions may be executed to support one or more aspects of the functionality described in this disclosure.

Although low-to-high stimulation parameter scans have generally been presented herein, other manners of systematically changing a stimulation parameter are also contemplated and could be substituted. For example, a scan could go from high-to-low or successive presentations of several prescribed frequencies (but not necessarily in ascending or descending order) could be executed.

Although the present disclosure generally discusses supportive stimulation to promote a type of brain activity, it is contemplated that these techniques could be applicable to suppressive therapeutic applications. Suppressive therapeutic applications include delivering stimulation to the brain to suppress unwanted and usually detrimental brain activity of a brain area. For example, beta band oscillatory frequencies can be associated with impaired motor function and symptoms of Parkinson's disease. A device may be employed to deliver stimulation to suppress any dominant beta band oscillatory frequencies. For example, a scan of stimulation that varies a stimulation frequency parameter, as discussed herein, can be performed while beta band frequencies (or other bioelectrical oscillation parameter) are monitored, techniques for scanning through stimulation frequencies of a frequency band and monitoring being discussed herein. The one stimulation frequency that is associated with the greatest suppression of a biomarker associated with a brain condition, such as the largest power for a frequency in the beta frequency band, can be set as the stimulation frequency for therapy delivery and the therapy can subsequently be delivered. Moreover, the aspects of identifying stimulation frequencies that evoke certain responses, scanning through one or more parameters, and/or updating stimulation frequency parameters, as discussed in connection with FIGS. 1-4, can be applied to setting appropriate parameters for suppressive stimulation of unwanted bioelectrical oscillations.

It will be appreciated that the various techniques, features, and components discussed herein in various embodiments are applicable to various other embodiments in different configurations and combinations, as the present disclosure makes use of examples to illustrate options which are not limited to the specific embodiments presented. As such, each example embodiment should be understood to be selectively combinable and modifiable in view of the other embodiments presented herein.

We claim:

1. A method for configuring therapy, comprising:
    delivering electrical stimulation to a brain at a plurality of different stimulation frequencies;
    sensing one or more bioelectrical signals;
    identifying a bioelectrical resonance response of the brain to the electrical stimulation, the bioelectrical resonance response identified based on a parameter of oscillation determined from the one or more sensed bioelectrical signals and indicative of resonance of an area of the brain to one stimulation frequency of the plurality of stimulation frequencies;
    setting a stimulation frequency parameter for a therapy based on the identified bioelectrical resonance response, wherein the stimulation frequency parameter is set at or near the one stimulation frequency; and
    delivering the therapy to the brain using the set stimulation frequency parameter, wherein each of delivering electrical stimulation, sensing, identifying, setting, and delivering the therapy are performed at least in part by control circuitry wherein the bioelectrical resonance response is induced by the electrical stimulation.

2. The method of claim 1, wherein delivering the electrical stimulation comprises delivering the electrical stimulation for each of a plurality of stimulation intervals, the electrical stimulation being delivered for each stimulation interval of the plurality at a respective stimulation frequency of the plurality of different stimulation frequencies.

3. The method of claim 1, wherein:
    the parameter of oscillation comprises a duration of a bioelectrical oscillation response to the electrical stimulation; and
    identifying the bioelectrical resonance response comprises determining which stimulation frequency of the plurality of different stimulation frequencies is associated with the longest duration of bioelectrical oscillatory response.

4. The method of claim 1, wherein:
    the parameter of oscillation comprises a power value in the frequency domain; and
    identifying the bioelectrical resonance response comprises determining which stimulation frequency of the plurality of different stimulation frequencies is associated with the highest power value.

5. The method of claim 1, wherein the electrical stimulation is delivered to the subthalamic nucleus, and the area of the brain for which the bioelectrical resonance response is identified is the subthalamic nucleus.

6. The method of claim 1, wherein the therapy is delivered to treat a movement disorder.

7. The method of claim 1, wherein the plurality of different stimulation frequencies comprise a range of frequencies within the gamma frequency band.

8. The method of claim 1, wherein setting the stimulation frequency parameter for the therapy comprises setting the stimulation frequency parameter at the one stimulation frequency.

9. The method of claim 1, wherein setting the stimulation frequency parameter near the one stimulation frequency comprises setting the stimulation frequency parameter closer to the one stimulation frequency than to any other stimulation frequency of the plurality of different stimulation frequencies.

10. The method of claim 1, wherein delivering electrical stimulation to the brain at the plurality of different stimulation frequencies comprises delivering electrical stimulation to the brain at the plurality of different stimulation frequencies for each of a plurality of different stimulation amplitude values, and wherein the method further comprises setting a stimulation amplitude parameter of the therapy, the amplitude parameter being set at or slightly higher than the lowest amplitude value of the plurality of different stimulation amplitude values for which the bioelectrical resonance response was identified.

11. The method of claim 1, wherein delivering the electrical stimulation at the plurality of different stimulation frequencies comprises incrementally increasing or decreasing stimulation frequency so as to scan delivery of the electrical stimulation through the plurality of different stimulation frequencies.

12. The method of claim 1, wherein the steps of delivering the electrical stimulation, sensing, identifying the bioelectrical resonance response, and setting the stimulation frequency parameter are repeated according to a schedule or a trigger to update the stimulation frequency parameter.

13. The method of claim 1, further comprising monitoring for an endogenous bioelectrical oscillation of the patient in a particular frequency band, wherein the steps of delivering the electrical stimulation and identifying the bioelectrical resonance response are performed based on the endogenous bioelectrical oscillation not being present in the particular frequency band during the monitoring.

14. The method of claim 1, wherein the stimulation frequency parameter induces self-supporting activation of a brain that continues for a duration following stimulation.

15. The method of claim 1, wherein the bioelectrical resonance response comprises an oscillatory change responsive to delivery of the electrical stimulation at the one frequency and wherein the oscillatory change is not present at other ones of the plurality of different stimulation frequencies.

16. The method of claim 1, wherein oscillatory activity that is present before stimulation is not indicative of the bioelectrical resonance response.

17. The method of claim 1, wherein oscillatory activity that is present at multiple ones of the plurality of different stimulation frequencies is not indicative of the bioelectrical resonance response.

18. A system comprising:
one or more sensors configured to receive one or more bioelectrical signals indicative of brain activity;
a stimulation generator configured to deliver electrical stimulation to a brain; and
control circuitry configured to:
control the stimulation generator to deliver the electrical stimulation to a brain at a plurality of different stimulation frequencies;
identify a bioelectrical resonance response of the brain to the electrical stimulation, the bioelectrical resonance response identified based on a parameter of oscillation determined from the one or more bioelectrical signals and indicative of resonance of an area of the brain to one stimulation frequency of the plurality of stimulation frequencies;
set a stimulation frequency parameter for a therapy based on the identified bioelectrical resonance response, the stimulation frequency parameter set at or near the one stimulation frequency; and
control the stimulation generator to deliver the therapy to the brain using the set stimulation frequency parameter.

19. The system of claim 18, wherein the control circuitry is configured to control the stimulation generator to deliver the electrical stimulation for each of a plurality of stimulation intervals such that the electrical stimulation is delivered for each stimulation interval of the plurality at a respective stimulation frequency of the plurality of different stimulation frequencies.

20. The system of claim 18, wherein the parameter of oscillation comprises a duration of a bioelectrical oscillation response to the electrical stimulation, and wherein the control circuitry is configured to identify the bioelectrical resonance response by determining which stimulation frequency of the plurality of different stimulation frequencies is associated with the longest duration.

21. The system of claim 18, wherein the parameter of oscillation comprises a power value in the frequency domain, and wherein the control circuitry is configured to identify the bioelectrical resonance response by determining which stimulation frequency of the plurality of different stimulation frequencies is associated with the highest power value.

22. The system of claim 18, wherein the therapy comprises a movement disorder therapy.

23. The system of claim 18, wherein the plurality of different stimulation frequencies comprise a range of frequencies within the gamma frequency band.

24. The system of claim 18, wherein the control circuitry is configured to set the stimulation frequency parameter for the therapy at or near the one stimulation frequency by setting the stimulation frequency parameter for the therapy at the one stimulation frequency.

25. The system of claim 18, wherein the control circuitry is configured to set the stimulation frequency parameter for the therapy at or near the one stimulation frequency by setting the stimulation frequency parameter closer to the one stimulation frequency than to any other stimulation frequency of the plurality of different stimulation frequencies.

26. The system of claim 18, wherein the control circuitry is configured to:
control the stimulation generator to deliver electrical stimulation to the brain at the plurality of different stimulation frequencies by controlling the stimulation generator to deliver electrical stimulation to the brain at the plurality of different stimulation frequencies for each of a plurality of different stimulation amplitude values; and
set a stimulation amplitude parameter for the therapy by setting the amplitude parameter at or slightly higher than the lowest amplitude value of the plurality of different stimulation amplitude values for which the bioelectrical resonance response was identified.

27. The system of claim 18, wherein the control circuitry is configured to control the stimulation generator to deliver the electrical stimulation at the plurality of different stimulation frequencies by incrementally increasing or decreasing stimulation frequency so as to scan delivery of the electrical stimulation through the plurality of different stimulation frequencies.

28. The system of claim 18, wherein the control circuitry is configured to repeat the steps of delivering the electrical stimulation, identifying the bioelectrical resonance response, and setting the stimulation frequency parameter according to a schedule or a trigger to update the stimulation frequency parameter.

29. The system of claim 18, wherein the control circuitry is configured to monitor for an endogenous bioelectrical oscillation of the brain in a particular frequency band using the one or more bioelectrical signals, wherein the control circuitry is configured to perform the steps of delivering the electrical stimulation, identifying the bioelectrical resonance response, and setting the stimulation frequency parameter only if the endogenous bioelectrical oscillation is not present in the particular frequency band.

30. The system of claim 18, wherein the stimulation frequency parameter induces self-supporting activation of a brain that continues for a duration following stimulation.

31. The system of claim 18, wherein the bioelectrical resonance response comprises an oscillatory change responsive to delivery of the electrical stimulation at the one frequency and wherein the oscillatory change is not present at other ones of the plurality of different stimulation frequencies.

32. The system of claim 18, wherein oscillatory activity that is present before stimulation is not indicative of the bioelectrical resonance response.

33. The system of claim 18, wherein oscillatory activity that is present at multiple ones of the plurality of different stimulation frequencies is not indicative of the bioelectrical resonance response.

34. A system, comprising:
- means for delivering electrical stimulation to a brain at a plurality of different stimulation frequencies;
- means for sensing one or more bioelectrical signals;
- means for identifying a bioelectrical resonance response of the brain to the electrical stimulation, the bioelectrical resonance response identified based on a parameter of oscillation determined from the one or more sensed bioelectrical signals and indicative of resonance of an area of the brain to one stimulation frequency of the plurality of stimulation frequencies;
- means for setting a stimulation frequency parameter for a therapy based on the identified bioelectrical resonance response, wherein the stimulation frequency parameter is set at or near the one stimulation frequency; and
- means for delivering the therapy to the brain using the set stimulation frequency parameter, and
- wherein the bioelectrical resonance response is induced by the electrical stimulation.

\* \* \* \* \*